(12) United States Patent
Huo et al.

(10) Patent No.: US 10,818,074 B2
(45) Date of Patent: Oct. 27, 2020

(54) BONE SEGMENTATION AND DISPLAY FOR 3D EXTREMITY IMAGING

(71) Applicant: CARESTREAM HEALTH, INC., Rochester, NY (US)

(72) Inventors: Zhimin Huo, Pittsford, NY (US); Jing Zhang, Shanghai (CN); Hui Zhao, Pittsford, NY (US)

(73) Assignee: Carestream Health, Inc., Rochester, NY (US)

(*) Notice: Subject to any disclaimer, the term of this patent is extended or adjusted under 35 U.S.C. 154(b) by 203 days.

(21) Appl. No.: 16/108,170

(22) Filed: Aug. 22, 2018

(65) Prior Publication Data

US 2019/0175125 A1 Jun. 13, 2019

Related U.S. Application Data

(60) Provisional application No. 62/597,989, filed on Dec. 13, 2017.

(51) Int. Cl.

| | |
|---|---|
| *G06K 9/00* | (2006.01) |
| *G06T 15/08* | (2011.01) |
| *G06T 7/00* | (2017.01) |
| *A61B 6/00* | (2006.01) |
| *A61B 6/03* | (2006.01) |

(Continued)

(52) U.S. Cl.
CPC ............ *G06T 15/08* (2013.01); *A61B 6/032* (2013.01); *A61B 6/4085* (2013.01); *A61B 6/466* (2013.01); *A61B 6/505* (2013.01); *A61B 6/5205* (2013.01); *G06T 7/0012* (2013.01); *A61B 6/4429* (2013.01); *A61B 6/5258* (2013.01); *G06T 5/005* (2013.01); *G06T 17/00* (2013.01); *G06T 2207/10072* (2013.01); *G06T 2207/10081* (2013.01); *G06T 2207/30008* (2013.01)

(58) Field of Classification Search
None
See application file for complete search history.

(56) References Cited

U.S. PATENT DOCUMENTS

| | | |
|---|---|---|
| 5,270,926 A | 12/1993 | Tam |
| 5,999,587 A | 12/1999 | Ning et al. |
| 8,348,506 B2 | 1/2013 | Yorkston et al. |

(Continued)

OTHER PUBLICATIONS

L.A. Feldkamp et al., "Practical cone-beam algorithm," Journal of the Optical Society of America, vol. 1, pp. 612-619, Jun. 1984.

*Primary Examiner* — Wei Wen Yang

(57) ABSTRACT

A method acquires a reconstructed tomographic volume image of anatomy of a patient and constructs a primary axis for a bone of interest in the imaged anatomy. The method forms a sectioned image of the bone in the volume image according to a first plane that is defined to extend along the bone and to extend through two or more articular surfaces. A primary axis for the bone is estimated, wherein the primary axis is midway between outer edges of the bone image that intersect the first sectioning plane. The bone is sectioned in the volume image by a second plane that is orthogonal to the first plane and that extends through the estimated primary axis. The method recalculates the position of the constructed primary axis according to the sectioning of the bone by the second plane. The recalculated constructed primary axis for the bone of interest is displayed.

20 Claims, 26 Drawing Sheets

(51) Int. Cl.
　　　*G06T 5/00*　　　　(2006.01)
　　　*G06T 17/00*　　　(2006.01)

(56) References Cited

U.S. PATENT DOCUMENTS

| | | |
|---|---|---|
| 8,483,469 B2 | 7/2013 | Pavlovskaia et al. |
| 8,532,361 B2 | 9/2013 | Pavlovskaia et al. |
| 9,208,263 B2 | 12/2015 | Pavlovskaia et al. |
| 9,980,780 B2 | 5/2018 | Lang |
| 2012/0165820 A1* | 6/2012 | De Smedt ............ A61B 17/175 606/87 |
| 2013/0070984 A1 | 3/2013 | Shirasaka et al. |
| 2014/0328524 A1 | 11/2014 | Hu et al. |
| 2015/0178917 A1 | 6/2015 | Yang et al. |
| 2017/0258526 A1* | 9/2017 | Lang .................. A61B 17/1703 |

* cited by examiner

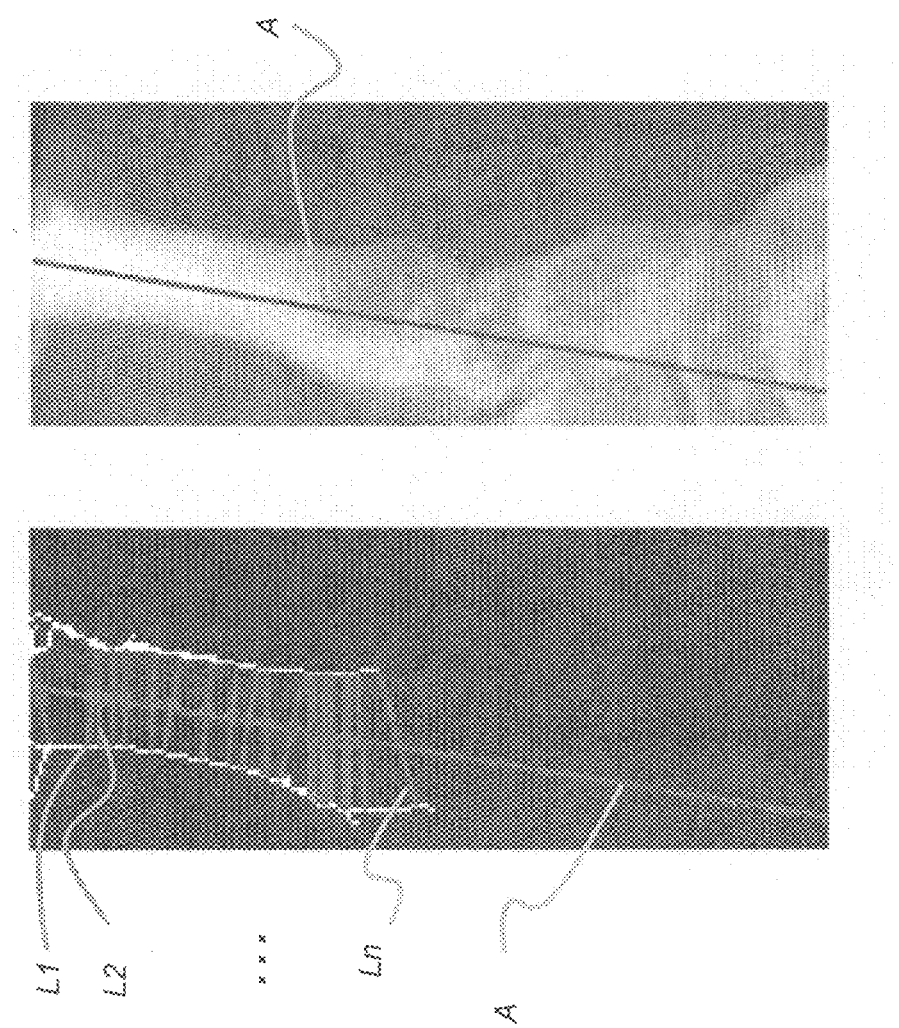

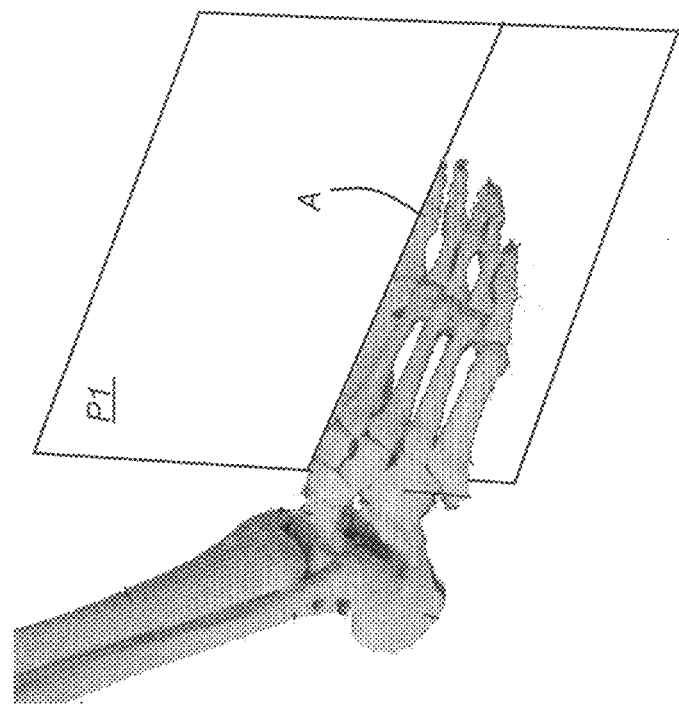
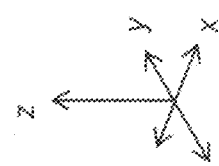
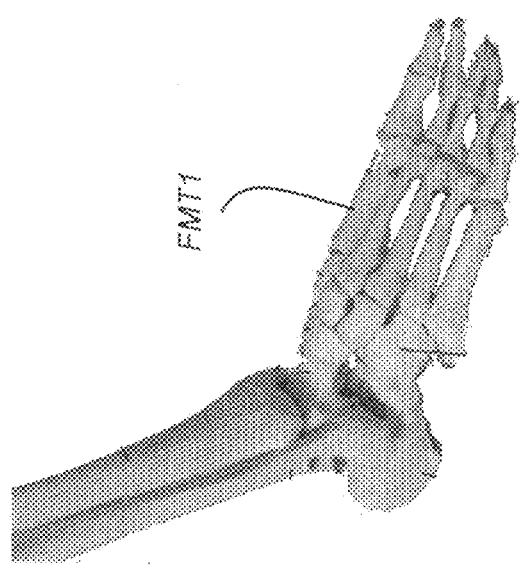
FIG. 4A
FIG. 4B

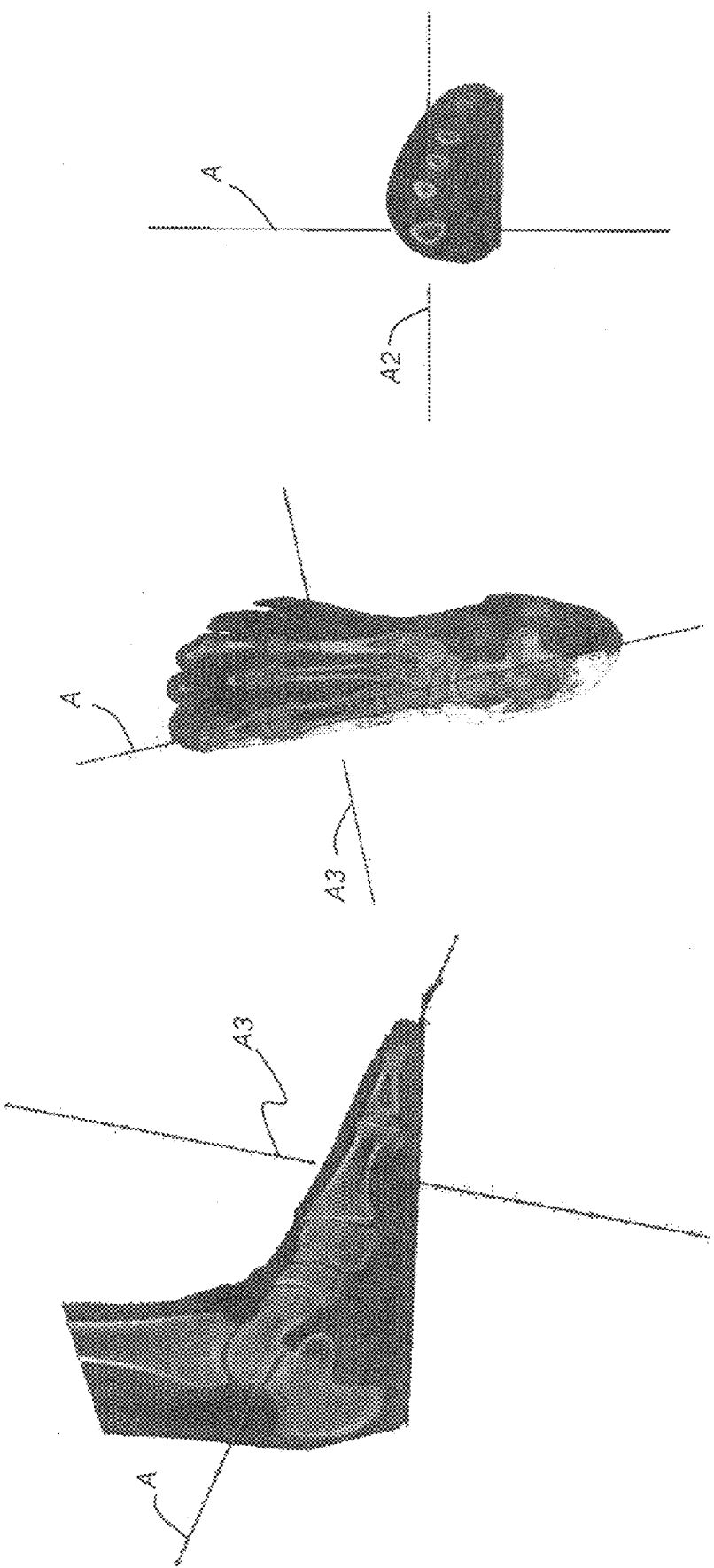

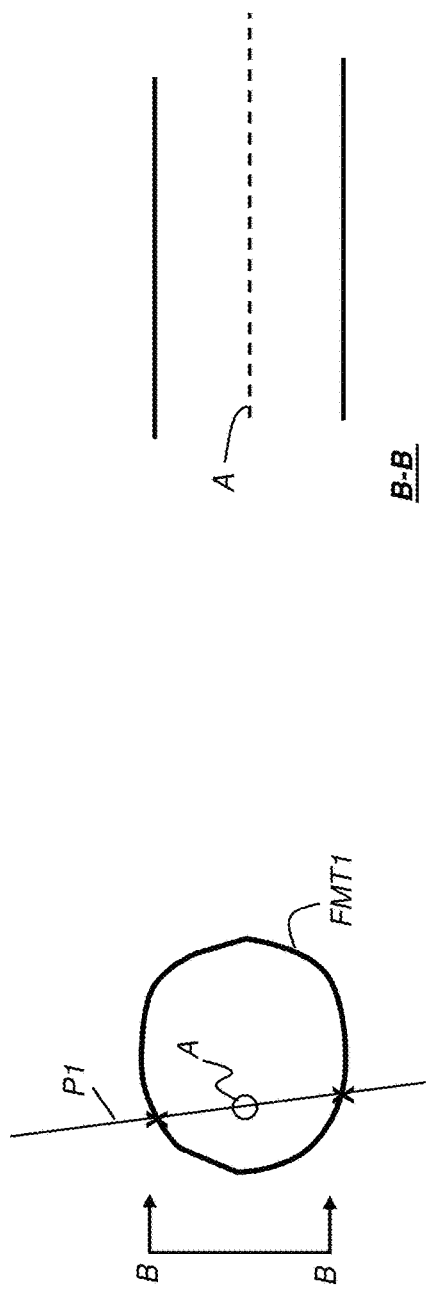
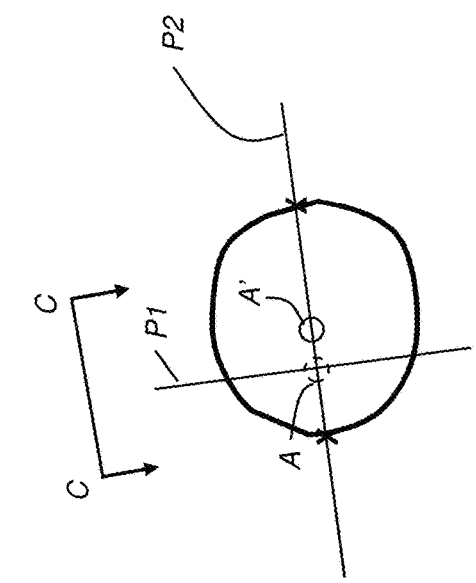
FIG. 6A
FIG. 6B
FIG. 6C
FIG. 6D

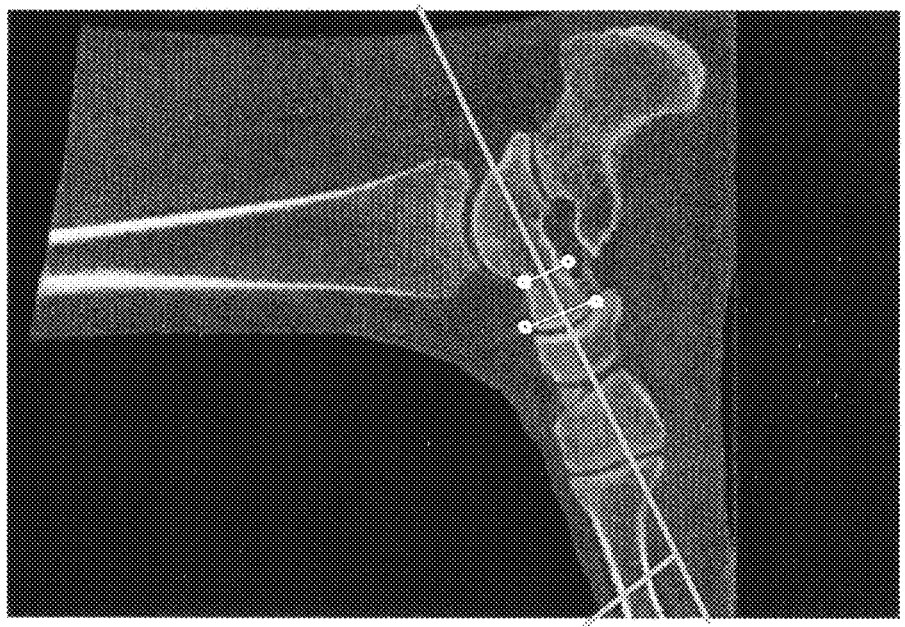
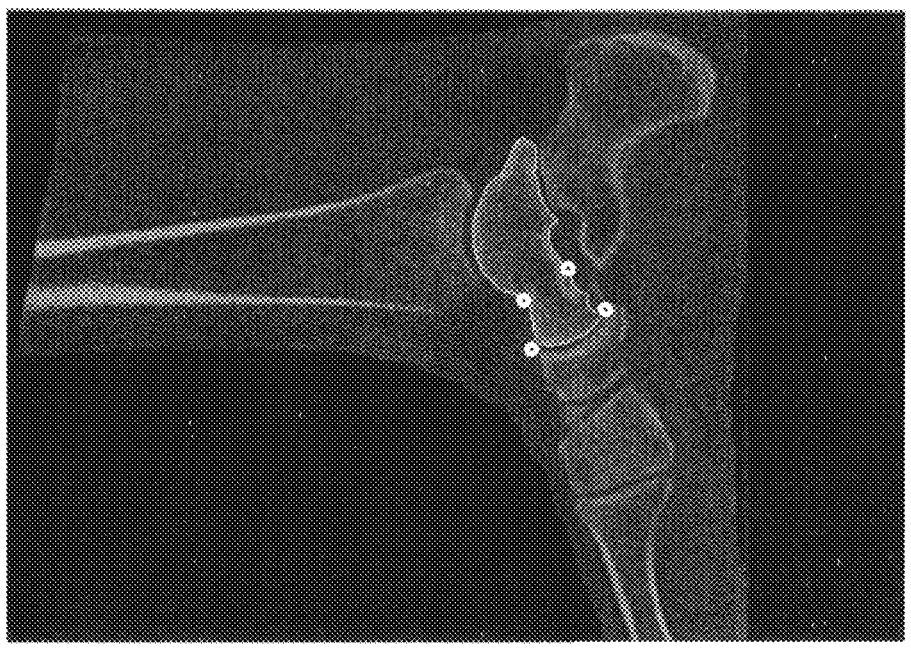
FIG. 7D

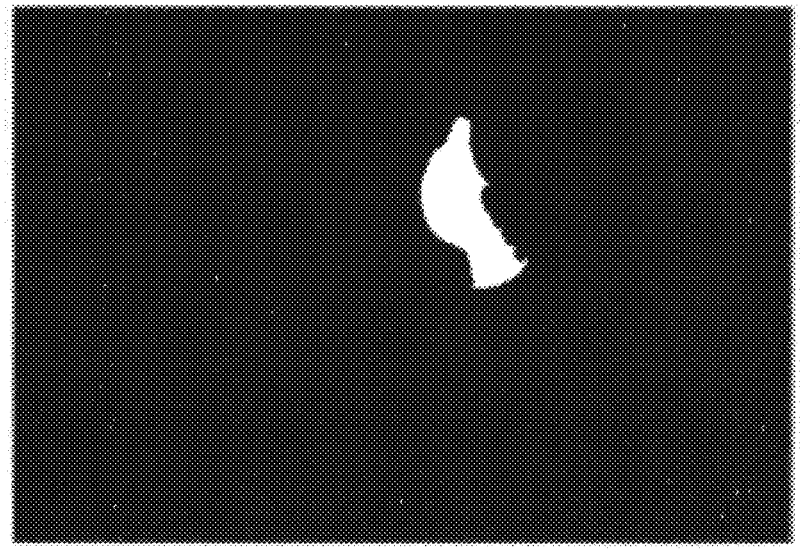
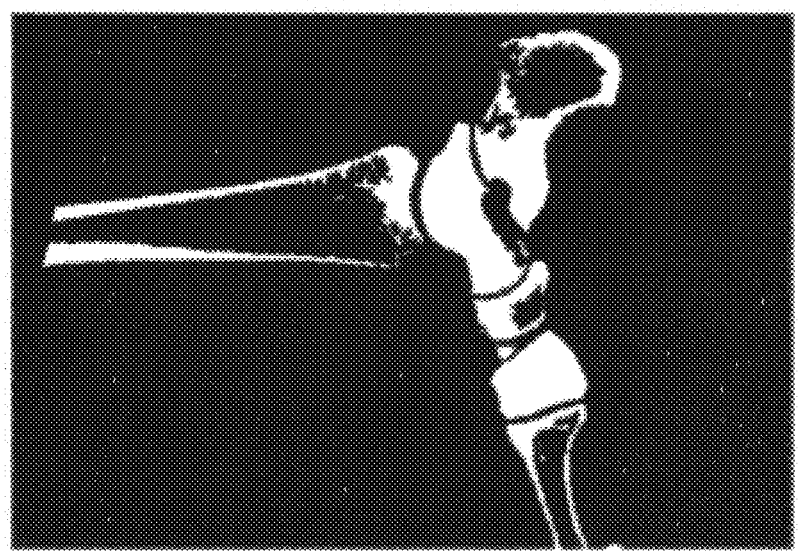
FIG. 16

BONE SEGMENTATION AND DISPLAY FOR 3D EXTREMITY IMAGING

CROSS REFERENCE TO RELATED APPLICATIONS

This applications claims priority to U.S. Provisional application U.S. Ser. No. 62/597,989, provisionally filed on Dec. 13, 2017, entitled "BONE SEGMENTATION AND DISPLAY FOR 3D EXTREMITY IMAGING", in the names of Huo et al, incorporated herein in its entirety.

FIELD OF THE INVENTION

The invention relates generally to the field of diagnostic imaging and in particular to Cone-Beam Computed Tomography (CBCT) imaging of extremities. More specifically, the invention relates to a method for improved segmentation techniques for structures and surfaces from the reconstructed image and improved detection of feature points for morphometric characterization of bone structures in 3D image space.

BACKGROUND OF THE INVENTION 3D volume imaging is a diagnostic tool that offers significant advantages over earlier 2D radiographic imaging techniques for evaluating the condition of internal structures and organs. 3D imaging of a patient or other subject has been made possible by a number of advancements, including the development of high-speed imaging detectors, such as digital radiography (DR) detectors that enable multiple images to be taken in rapid succession.

In particular, knowledge of foot morphometry, including measurement of shape, angular, and dimensional characteristics, is useful for analyzing proper foot structure and function. Foot structure is important for a number of reasons. The foot anthropometric and morphology phenomena are analyzed together with various biomechanical descriptors in order to fully characterize foot functionality.

Cone beam computed tomography (CBCT) or cone beam CT technology offers considerable promise as one type of diagnostic tool for providing 3D volume images. Cone beam CT systems capture volume data sets by using a high frame rate flat panel digital radiography (DR) detector and an x-ray source, typically affixed to a gantry that revolves about the object to be imaged, directing, from various points along its orbit around the subject, a divergent cone beam of x-rays toward the subject. The CBCT system captures projection images throughout the source-detector orbit, for example, with one 2D projection image at every degree increment of rotation. The projections are then reconstructed into a 3D volume image using various algorithmic techniques. Among the most common methods for reconstructing the 3D volume image are filtered back projection (FBP) approaches. An exemplary reconstruction approach is described, for example, in the paper by L. A. Feldkamp, L. C. Davis, and J. W. Kress, entitled "Practical cone-beam algorithm," *Journal of the Optical Society of America*, vol 1, pp. 612-619, June, 1984.

Although 3D images of diagnostic quality can be generated using CBCT systems and technology, a number of technical challenges remain. One continuing technical problem particular to extremity volume imaging relates to segmentation and accurate feature identification for measurement and morphometric characterization. Accurate segmentation techniques would allow the practitioner to isolate a particular bone structure from surrounding structures and to examine shape, surface quality, dimensions, angular, and spatial characteristics. This can be valuable with extremity imaging where numerous bone structures fit together and cooperate for posture, movement, balance, dexterity, and other functions.

As is well known, bones of the extremities, such as hand, feet and ankles, and knees, have complex structure and spatial arrangement. Metrics related to the spatial position of these bones, their dimensions, their relative angular relationships, disposition of interface surfaces, and other characteristics can be useful in diagnosis and treatment of a number of conditions. Thus, it would be beneficial to provide methods that allow improved segmentation of bone features of the extremities to allow measurement and analysis.

SUMMARY OF THE INVENTION

It is an object of the present invention to advance the art of volume imaging and provide improved segmentation and measurement for bone structures, particularly for extremities and joints.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method comprising: acquiring a reconstructed tomographic volume image of anatomy of a patient; constructing a primary axis for a bone of interest in the imaged anatomy by: (i) forming a sectioned image of the bone in the volume image according to a first plane that is defined to extend along the bone and to extend through two or more articular surfaces; (ii) estimating a primary axis for the bone wherein the primary axis is midway between outer edges of the bone image that intersect the first sectioning plane; (iii) sectioning the bone in the volume image by a second plane that is orthogonal to the first plane and that extends through the estimated primary axis; (iv) recalculating the position of the constructed primary axis according to the sectioning of the bone by the second plane; and displaying the recalculated constructed primary axis for the bone of interest.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 3E shows the use of multiple line segments for identifying a primary axis.

FIG. 4A shows a volume reconstruction of a foot.

FIG. 4B shows construction of an initial axis for bone segmentation.

FIG. 5A shows a side view of the foot, relative to planes shown in FIG. 4B.

FIG. 5B shows an axial view of the foot.

FIG. 5C shows a sectioned view of the foot by a plane.

FIGS. 6A through 6D show steps in iterative axis reconstruction.

FIG. 7D shows another example of feature points and geometric features that can be used for axis construction.

FIG. 16 shows segmentation examples for a joint that can be obtained using methods of the present disclosure.

DETAILED DESCRIPTION OF THE INVENTION

Figure 1:
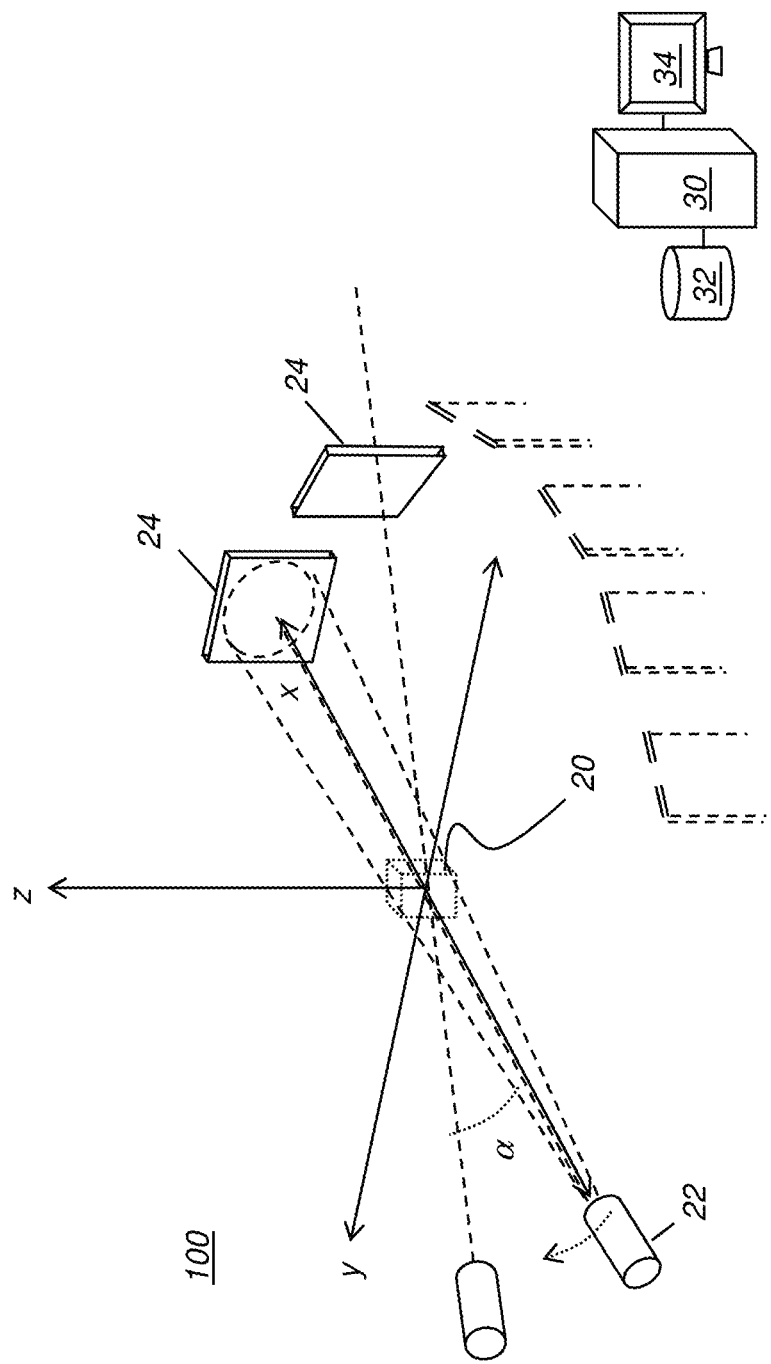
FIG. 1 is a block diagram schematic that shows how projection images are obtained.

The following is a detailed description of preferred embodiments of the invention, reference being made to the drawings in which the same reference numerals identify the same elements of structure in each of the several figures.

In the drawings and text that follow, like components are designated with like reference numerals, and similar descriptions concerning components and arrangement or interaction of components already described are omitted. Where they are used, the terms "first", "second", "third", and so on, do not necessarily denote any ordinal or priority relation, but are simply used to more clearly distinguish one element from another.

In the context of the present disclosure, the term "volume image" is synonymous with the terms "3Dimensional image" or "3D image". Embodiments of the present disclosure are particularly well suited for suppressing the types of metal artifacts that occur in 3D volume images, including cone-beam computed tomography (CBCT) as well as fan-beam CT images. However, it should be noted that the artifact reduction approach described herein is also applicable for 2D radiographic images, as described in more detail subsequently.

For the image processing steps described herein, the terms "pixels" and "pixel data" for picture image data elements, conventionally used with respect 2D imaging and image display, and "voxels" for volume image data elements, often used with respect to 3D imaging, can be used interchangeably. It should be noted that the 3D volume image is itself synthesized from image data obtained as pixels on a 2D sensor array and displays as a 2D image that is rendered from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels.

The term "set", as used herein, refers to a non-empty set, as the concept of a collection of elements or members of a set is widely understood in elementary mathematics. The terms "subset" or "partial subset", unless otherwise explicitly stated, are used herein to refer to a non-empty proper subset, that is, to a subset of the larger set, having one or more members, but not containing every member of the full set. A "proper subset" of set S is strictly contained in set S and excludes at least one member of set S. A "partition of a set" is a grouping of the set's elements into non-empty subsets so that every element is included in one and only one of the subsets. Two sets are "disjoint" when they have no element in common.

In computed tomography including CBCT, the term "projection image" usually refers to a 2D image that is acquired from a 3D object. A set of 2D radiographic projection images is acquired and processed in order to reconstruct a 3D volume. It should be noted, however, that an alternate type of 2D projection image can also be generated by projecting through a reconstructed 3D volume. This process is performed, for example, as "forward projection" in various types of iterative reconstruction techniques. That is, once the 3D volume has been reconstructed from the original acquired radiographic 2D projection images, the 3D volume can, in turn, be used as a type of "object" for generation of a computed projection image. In order to distinguish between these two types of projection image, the descriptive term "acquired" is used to specify actual 2D projection images that are provided from the digital radiography (DR) detector. The descriptive term "generated" is used to specify a calculated 2D projection image that is formed from the reconstructed 3D volume or from some portion of the reconstructed volume image data, such as from one or more slices of the reconstructed volume.

CBCT imaging apparatus and the imaging algorithms used to obtain 3D volume images using such systems are well known in the diagnostic imaging art and are, therefore, not described in detail in the present application. An exemplary medical cone-beam CT imaging system for extremity exams is the Carestream OnSight 3D Extremity System from Carestream Health, Inc., Rochester, N.Y. Extremity imaging CBCT apparatus is also described in U.S. Pat. No. 8,348,506 (Yorkston) entitled "EXTREMITY IMAGING APPARATUS FOR CONE BEAM COMPUTED TOMOGRAPHY", incorporated herein in its entirety. Some exemplary algorithms and approaches for forming 3D volume images from the source 2D projection images that are obtained in operation of the CBCT imaging apparatus can be found, for example, in the Feldkamp et al. paper noted previously and in the teachings of U.S. Pat. No. 5,999,587 (Ning) entitled "METHOD OF AND SYSTEM FOR CONE-BEAM TOMOGRAPHY RECONSTRUCTION" and of U.S. Pat. No. 5,270,926 (Tam) entitled "METHOD AND APPARATUS FOR RECONSTRUCTING A THREE-DIMENSIONAL COMPUTERIZED TOMOGRAPHY (CT) IMAGE OF AN OBJECT FROM INCOMPLETE CONE BEAM DATA". Reference is also made to commonly assigned U.S. 2015/0178917 (Yang) entitled "METAL ARTIFACTS REDUCTION FOR CONE BEAM CT USING IMAGE STACKING".

In conventional applications, a computer or other type of dedicated logic processor for obtaining, processing, and storing image data is part of the CBCT system, along with one or more displays for viewing image results. A computer-accessible memory is also provided, which may be a memory storage device used for longer term storage, such as a device using magnetic, optical, or other data storage media. In addition, the computer-accessible memory can comprise an electronic memory such as a random access memory (RAM) that is used for shorter term storage, such as employed to store a computer program having instructions for controlling one or more computers to practice the method according to the present disclosure.

In order to more fully understand the methods of the present invention and the problems addressed, it is instructive to review principles and terminology used for CBCT image capture and reconstruction. Referring to the perspective view of FIG. 1, there is shown, in schematic form and using enlarged distances for clarity of description, the activity of a conventional CBCT imaging apparatus 100 for acquiring the individual 2D projection images that are used to form a 3D volume image. A cone-beam radiation source 22 directs a cone of radiation toward a subject 20, such as a patient or other subject. A sequence of acquired 2D projection images is obtained in rapid succession at varying angles about the subject, such as one image at each 1-degree angle increment in a 200-degree orbit. A digital radiography (DR) detector 24 is moved to different imaging positions about subject 20 in concert with corresponding orbital movement of radiation source 22.

FIG. 1 shows a representative sampling of DR detector 24 positions to illustrate how these acquired projection images are obtained relative to the position of subject 20. Once the needed 2D projection images are captured in this sequence, a suitable imaging algorithm, such as filtered back projection (FBP) or other conventional technique, is used for reconstruction of the 3D volume image. Image acquisition and program execution for generating the reconstructed 3D image are performed by a computer 30 or by a networked group of computers 30 in image data signal communication with DR detectors 24. Image processing and storage is performed using a computer-accessible memory 32. The reconstructed 3D volume image can be rendered for from a range of angles for presentation on a display 34.

In the context of the present disclosure, the term "segmentation" has the broad meaning that is generally understood by those skilled in the image processing arts. The act of segmenting a structure within the volume image labels and partitions the image content in some way so that one or more sets of voxels are grouped according to the structure(s) or feature(s) they represent. Thus, for a volume image of the foot, for example, segmentation can be used to isolate one or more metatarsals for more detailed examination. This would allow the practitioner to view surfaces that would otherwise be hidden or obscured by adjacent bone structures.

Segmentation allows the practitioner to view individual features such as interfacing and articular surfaces of bones and allows generation of metrics related to dimension, spatial position, and relative angular relationships that can be useful in diagnosis and treatment of a number of conditions. The complex structure of human extremities such as hands, feet, ankles, knees, and elbows makes it difficult to automate the segmentation process that would allow accurate spatial characterization of a single bone or bone surface.

Among the challenges to bone segmentation for ankles, knees, and other limbs is the difficulty of accurately combining information for bone features whose cross-sectional aspects differ pronouncedly from each other in axial, sagittal, and coronal views. That is, considered from different orthogonal perspectives, the bone shapes can be dramatically different in 2D representation and it can be difficult to relate information about the same bone of interest from different orthogonal views. Embodiments of the present disclosure address the segmentation problem and provide solutions for more accurate visualization and measurement of complex skeletal structures.

Conventional segmentation techniques apply a sequence of pixel or voxel classification and labeling techniques that group data elements to define the shape, contour, and spatial orientation of the bone feature. The Applicants have noted that existing methods have not addressed aspects of bone structure that are particularly useful for extremity imaging, particularly for identifying bone axes and their spatial and related geometric relationships, and for characterizing interaction at articular or joint surfaces. Embodiments of the present disclosure are directed to segmentation approaches that remedy this deficiency and provide improved joint segmentation and useful structural metrics for assessing joint relationships and interaction. The Applicants have recognized, for example, that bone axis information, that must often be separately derived after results are obtained when using conventional segmentation techniques, can be of particular value earlier in image processing and can even be used to assist segmentation and joint characterization.

Figure 2:
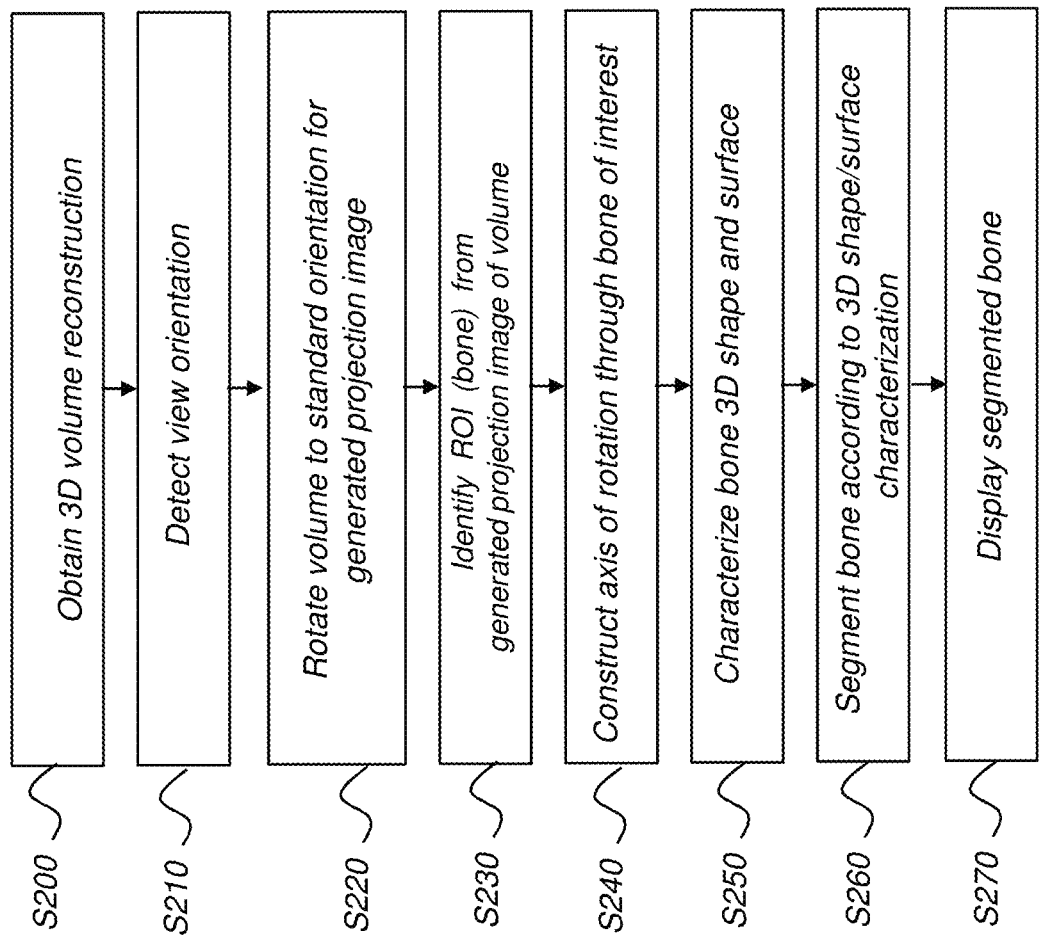
FIG. 2 is a logic flow diagram that gives a sequence for extremity segmentation according to an embodiment.

The logic flow diagram of FIG. 2 gives a sequence for extremity segmentation according to an embodiment. In a volume acquisition step S200, a previously reconstructed 3D volume image of an extremity is acquired. An orientation identification step S210 detects view orientation and coordinates that are useful for subsequent viewing and analysis. An orientation step S220 then determines which view of the reconstructed volume is most appropriate for the bone feature of interest and adjusts the view to provide a useful orientation for the generated 2D projection image from the reconstructed 3D volume. For example, orientation step S220 can work systematically using stored information for each successive bone in a foot or hand image. A projection step S230 then determines the region of interest (ROI) and, based on the bone type that is the ROI, generates an appropriate projection image view for use in initial processing steps. The generated projection image that is obtained is formed by considering a 2D image of the reconstructed volume image data from the particular angle that is determined in step S220 to be advantageous for the anatomy and bone(s) of interest.

Embodiments of the present disclosure can utilize different views of the reconstructed volume image to execute various steps in the processing sequence of FIG. 2. As described in more detail subsequently, step 230 and related processing steps may generate or use one of the following:

(i) Projection image generated as a projection through the complete volume of the reconstructed anatomy of interest. This type of image is obtained as a type of projection through the full reconstructed volume, as noted previously, at an appropriate projection angle. The full-volume generated projection image can be most useful for initial detection of a bone ROI and, when taken at the proper acquisition angle, can provide a starting point for an iterative axis determination, as described in more detail subsequently.

(ii) Projection image through a slab of slices. This type of partial volume image is a generated projection of part of the reconstructed volume, formed as a stacking or slab of parallel slices.

(iii) Single slice of the volume, obtained as a generated projection image by "cutting" the volume along a plane that is at a suitable orientation.

Continuing with the FIG. 2 sequence, an axis construction step S240 provides an approximation of a primary axis that can be used for segmentation processing according to an embodiment of the present disclosure.

It should be noted that it can be of diagnostic value to indicate and highlight the primary axis of a bone within a 3D volume image. Information about the primary axis can allow the practitioner to analyze condition of a bone or joint more accurately, such as to more accurately visualize the interaction of bones along articular surfaces during patient movement. Axis construction for measurement and display is described in more detail subsequently.

A surface characterization step S250 then uses analysis of the 3D volume image according to the identified primary axis to locate the surface of the bone feature of interest, with particular emphasis on articular surfaces at or near bone joints. A segmentation step S260 can then be executed to perform segmentation processing using the results of surface characterization step S250. A display step S270 then allows rendering of the segmented bone on the display.

Detailed description of some of the significant steps of the FIG. 2 sequence follows.

Orientation Step S220

Figure 3B:
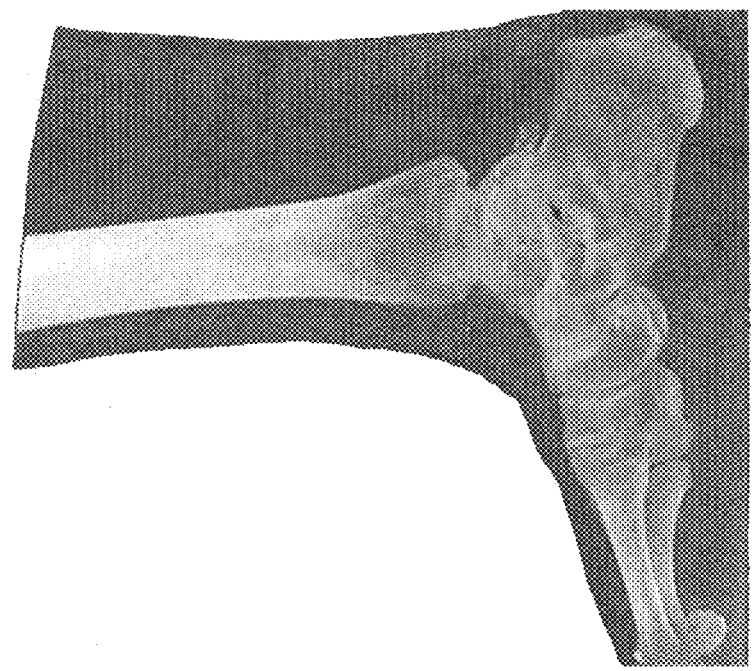
FIG. 3B shows a side view of a portion of a foot.
Figure 3A:
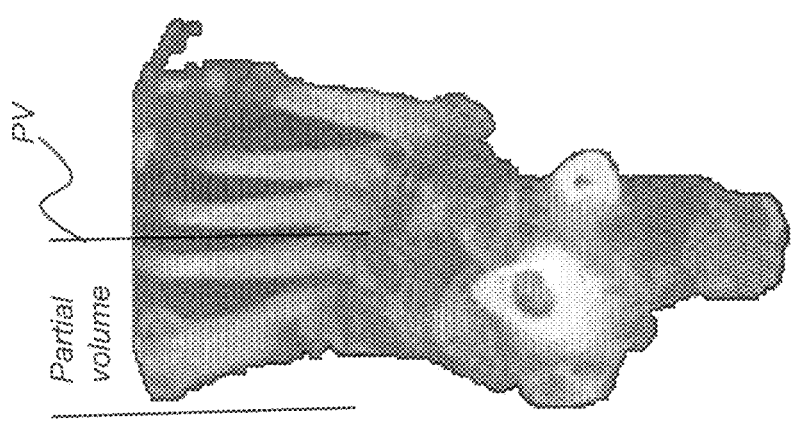
FIG. 3A shows an exemplary volume reconstruction used for subsequent examples.

Orientation step S220 in the FIG. 2 sequence can help to simplify the processing sequence for limb segmentation by using a well-defined generated projection view of the reconstructed image volume as a starting point. By way of example, FIG. 3A shows an axial, top-down, full-volume projection image generated using a projection through the reconstructed volume of the foot, ankle, and related structures. In this example, a generated projection from an axial view provides a useful image that shows a substantial number of bone features of this limb. It can be appreciated that the axial view is particularly well-suited for clear identification of metatarsal bones and related structures. On the other hand, this same view generally offers poor visibility of the talus or calcaneus, which appears more clearly in the side view of FIG. 3B.

As this example shows, the angle that is suitable for initial segmentation processing of different bone features can vary. For some portions of the skeletal anatomy, such as forward portions of the toes and hand for example, axial orientation as shown in FIG. 3A works most successfully; other portions can use orientation with respect to other angles. FIG. 3B shows a sagittal generated projection through a slab of slices, as described previously, of value for segmentation of the talus or calcaneous bones, for example. This projection view shows only that portion of the foot delineated in FIG. 3A.

Orientation step S220 of FIG. 2 can use a priori information based on the anatomy that is of interest for the volume imaging exam. The a priori information can include information obtained using an atlas or using other stored data as a guideline to bone identification and axis construction, for example.

Axis Construction Step S240

Still referring to the sequence of FIG. 2, once the preferred orientation for the bone or limb is provided, axis construction step S240 helps to identify an axis that serves as a basis for subsequent surface contour and feature characterization needed for accurate segmentation. Axis identification for neighboring bones also has value for showing how related bones interact, indicating various patient conditions that can be caused by poor relative positioning of bones with respect to their interfaces at articular surfaces. 3D visualization of the primary axis of bones at a joint can be particularly valuable for analysis of patient movement and sources of discomfort, for example.

As the example generated forward projection of the ankle in FIG. 3A shows, axis identification is not straightforward and a number of decisions must be made as to what features are used to define end-points or any two points needed to define the axis direction and extent. The top-down generated projection image of FIG. 3A and side view generated projection image of FIG. 3B show another difficulty with axis definition: the axis must ultimately be specified using 3D coordinates, and no two axes for bones of extremities are likely to be in parallel with respect to both axial and sagittal views.

Aspects of axis identification can include the following:

(i) Axis position is most advantageous when axes are constructed through point(s) on articular surface(s) of the bone. For reasons described in more detail subsequently, axis definition is of particular value for characterizing the contour of articular surfaces.

(ii) Axis construction can be an iterative process, with improved axis position obtained with each iteration, as described in more detail subsequently.

Initial positioning of the axis A is an estimate that can be based on a priori information about the limb that is imaged or can be from a standard reference, such as from an atlas, for example. Initially, a top-down generated projection as in FIG. 3A or a sagittal projection as in FIG. 3B can be used for initial axis positioning, depending on the bone of interest. The generated projection image may be full-volume, as in FIG. 3A, or a partial volume, formed from a partial subset of volume image slices as shown in FIG. 3B. FIG. 3A indicates the partial volume PV, including first and second metatarsals, that is used in the example of FIG. 3B.

Figure 3C:
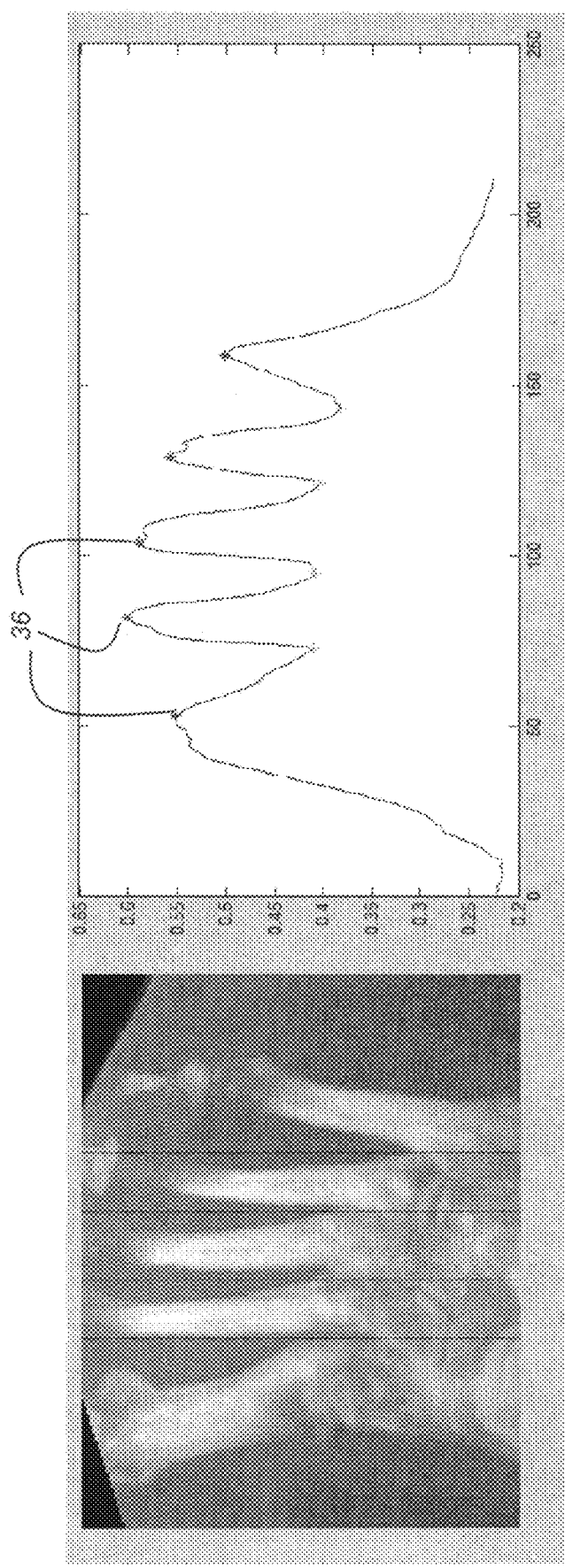
FIGS. 3C and 3D show graphs for generating an initial approximation of an axis for bone segmentation.
Figure 3D:
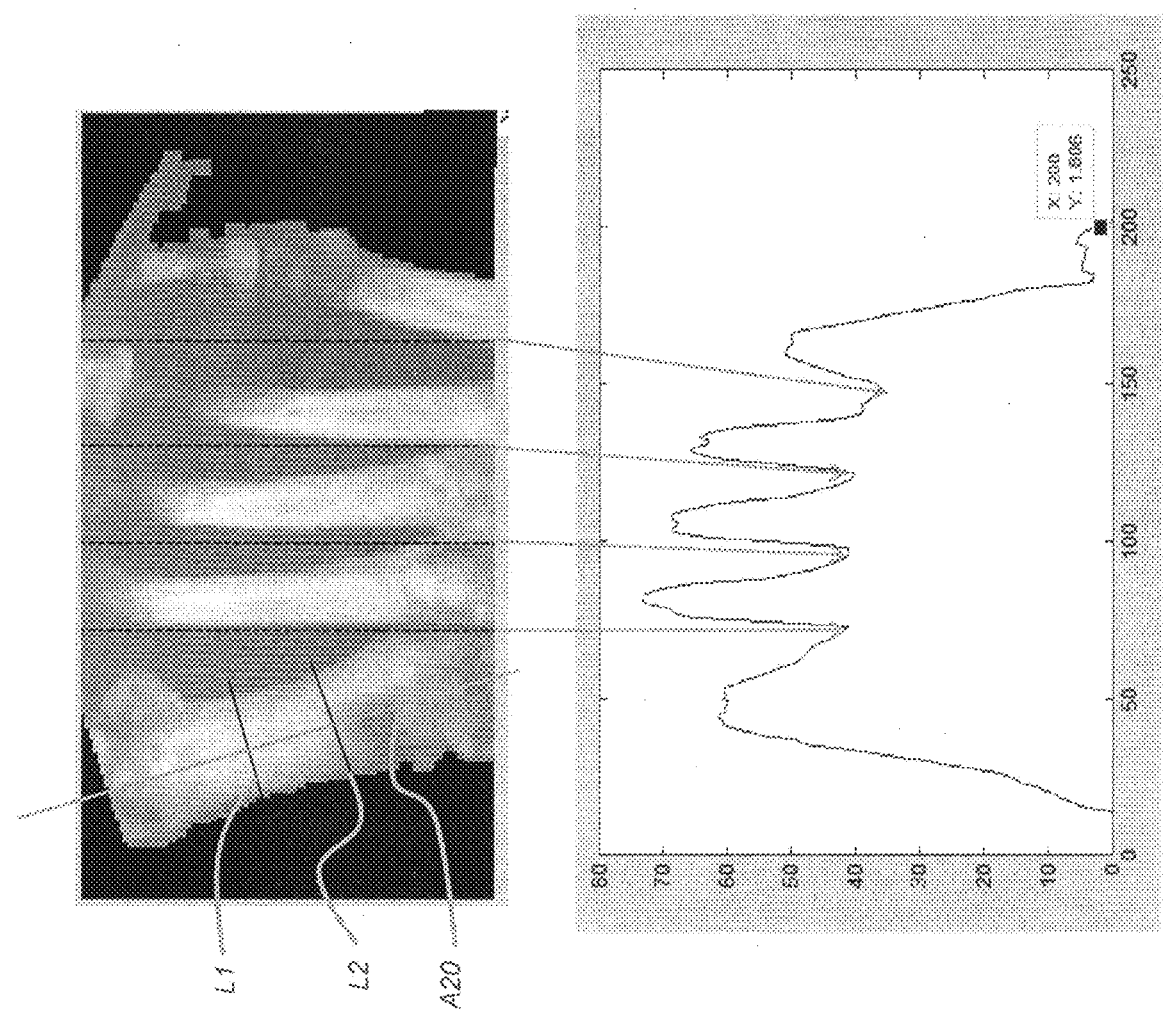

The graphs of FIGS. 3C and 3D show one method for initial approximation of an axis for any of the metatarsals. The graphs given in these figures show the accumulated or maximum intensity values along corresponding columns of the image data for the metatarsal portion of the ankle projection image. As these graphs show, peak and valley values of accumulated intensity correspond with some accuracy to the bone features in the vertical (columnar) presentation that is shown. It can be appreciated that obtaining a suitable orientation is useful for accurate results when using accumulated intensity values in this manner.

As illustrated in FIG. 3C, peak points 36 corresponding to each metatarsal can be identified from analysis of the generated projection image data and alternately used to define one of the two points needed for identifying a corresponding axis through the metatarsal bone.

FIG. 3D shows analysis of a full-volume top-down axial generated projection image for initial axis positioning. Lines L1 and L2 are obtained by taking measurements across the neck or other suitable portion(s) of the bone and determining the shortest distance across the bone. Midpoints of lines L1 and L2 are used to define the initial axis A20.

FIG. 3E shows identification of a primary axis A constructed using multiple line segments L1, L2, . . . Ln, extended from edge to opposite edge across a bone. A suitable generated projection image can be used for this analysis. For axis identification using this method, midpoints of the extended line segments L1, L2, . . . Ln are calculated and an averaging used to obtain the best fit to line midpoints. Line segments extending from one edge of the bone to an opposite edge can be used; the segments need not be parallel to each other and may even intersect. Bone features can be used to help define end-points for the line segments.

Embodiments of the present disclosure can identify a bone axis, as a central or primary bone axis, using an iterative procedure that employs cutting or sectioning planes through the 3D volume reconstruction in order to determine and refine axis positioning in 3D. Once the axis is identified, additional processing can then be used for bone segmentation, allowing bone surfaces and articular surfaces at the joints to be segmented by working from the computed primary axis outward. Advantageously, the primary axis is located in 3D space, rather than merely in 2D display. This 3D presentation enables detection and display of the primary axis to be particularly useful for diagnostic purposes. The length of the primary axis can be measured and displayed, along with angular information related to the coordinate space of the imaged volume. Primary axes for different bones can be displayed, including values of relative angle measurement between two or more axes. For example, where two bones interface at a joint, their respective axes can be displayed simultaneously, along with angular values indicative of the geometric relationship between the bones. Angular values relative to orthogonal x, y, z axes can be computed and displayed. Zenith and azimuthal angles can be computed and used to identify axis orientation.

In order to better understand other methods for how axis A for a particular bone feature can be identified, it is instructive to consider the example given schematically in FIGS. 4A, 4B, 4C, and 4D and shown as a first metatarsal in graphic displays in FIGS. 5A, 5B, and 5C.

FIG. 4A is a perspective view of an exemplary reconstruction for a foot, showing the position of a first metatarsal FMT1. As represented in FIG. 4B, an axis A defines the position of a first sectioning plane P1, extending generally in the sagittal direction for the example shown. Using the arbitrarily assigned axis definitions shown, the "cut" or sectioning of the image volume provided by plane P1 identifies the x,y axis coordinate axes for the three-dimensional bone axis initially approximated at A. Plane P1 approximately bisects the first metatarsal FMT1 in the sagittal direction. In processing for metatarsals and other bones of the feet that extend outward from the ankle, initial plane P1 for axis determination is typically positioned on a full-volume top-down axial generated projection (as in FIG. 3A). Beginning with this plane positioning, subsequent sectioning planes can be positioned using slices or partial volume generated projections.

Figure 4D:
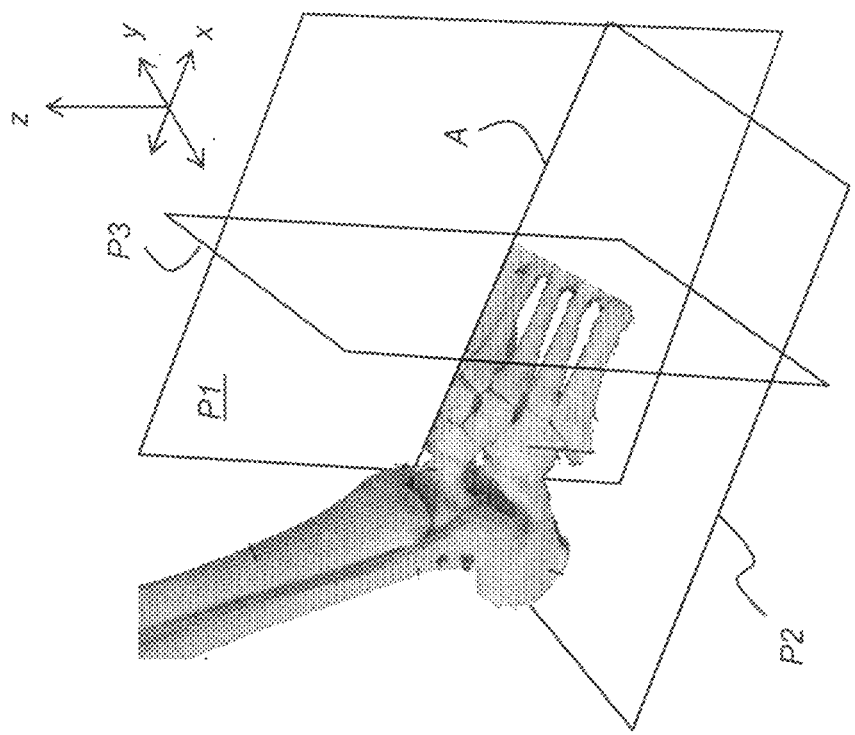
FIG. 4D shows a sectioning plane orthogonal to other planes used for axis refinement.
Figure 4C:
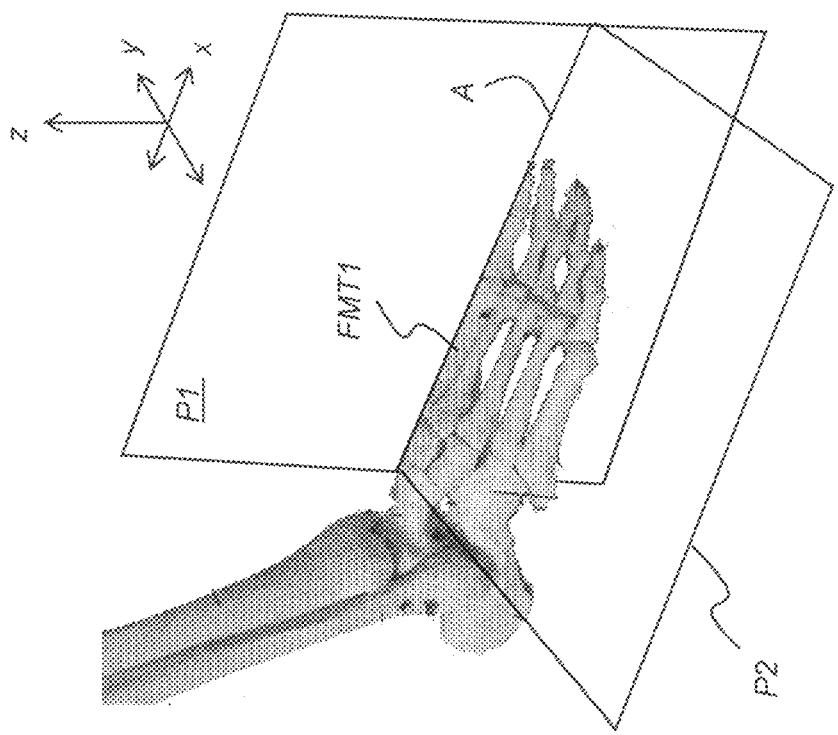
FIG. 4C shows use of an orthogonal plane for axis refinement.

FIG. 4C shows another plane P2 extended through the foot volume, oriented at an orthogonal to plane P1, with axis A at the intersection of planes P1 and P2. Plane P2 can determine a single slice of the reconstructed volume for axis determination. Positioning of plane P2 provides the needed z axis coordinates for 3D positioning. Using a pattern of mutually orthogonal sectioning planes as illustrated in FIGS. 4C and 4D allows iterative processing to derive the position of a primary axis for a bone of interest within a few sectioning iterations.

FIG. 4D shows a third plane P3 substantially orthogonal to both planes P1 and P2 and cross-sectionally dividing the foot, including a portion of first metatarsal FMT1.

FIG. 5A shows a sagittal slice of the foot, as sectioned in this direction by plane P1 in FIG. 4B.

FIG. 5B shows an axial slice of the foot, with axis A position and showing the position of a line A3 in plane A3 of FIG. 4D. The view of FIG. 5B is sectioned by plane P2 of FIG. 4C.

FIG. 5C shows a slice that is a sectioned view of the foot by plane P3 and shows a line A2 in plane P2.

The sequence shown in FIGS. 6A-6D show how the position of primary axis A can be constructed in an iterative manner using successive sectioning of the reconstructed volume by orthogonal planes P1 and P2 as shown in FIGS. 4B and 4C. For this example, bone FMT1 is outlined from the cross-sectional perspective of plane P3 of FIG. 4D, as shown in FIG. 5C. Steps in this process begin with an estimate of primary axis position from FIG. 4B and, within one or more iterations using an iterative sectioning technique, improve this estimate to more closely approximate the position of the primary axis for a bone feature.

Sectioning plane P1, represented by a line in FIG. 6A, approximately bisects the volume image reconstruction of the first metatarsal FMT1 in the axial direction, shown in a sagittal view. As long as the sectioning is at least somewhat accurate, the outline and volume distribution of the bone with respect to bisecting plane P1 that contains the axis A would be approximately symmetrical. Using this logic, the initial positioning of axis A according to plane P1 is along a sectioning plane that attempts to section the bone image into two substantially symmetrical portions. As shown in FIG. 6A, axis A, extending outward from the page in the perspective of this figure, is represented by a circle that is generally near the center of the bone from the cross-sectional view that is shown.

FIG. 6B shows a cross-sectional view of metatarsal FMT1 sectioning by plane P1 for a portion of the bone from a side (sagittal) view, orthogonal to the view of FIG. 6A. As can be seen from view B-B in FIG. 6B, an initial candidate axis A is generally best approximated halfway between the edges of the bone as sectioned.

FIG. 6C shows a subsequent sectioning along a second plane P2 that is orthogonal to plane P1 and that intersects initial candidate axis A. As FIGS. 6C and 6D show, this second sectioning yields an improved approximation of the primary axis, shown as axis A'. Using this method, with mutually orthogonal sectioning planes P1 and P2, two sectioning iterations can be all that is needed to identify a suitable primary axis for analysis of bone orientation and angle as well as for segmentation processing.

As noted previously, the initial position of sectioning plane P1 and, accordingly, of primary axis A obtained using this initial sectioning, is an approximation, largely dependent on the location and orientation of the sectioning planes and the bone shape with regard to articulating surfaces and the bone surfaces that extend between the articular surfaces. These factors relate to the bone type, as well as to other aspects such as patient age, sex, build, and bone condition.

It should be emphasized that the sectioning process operates on volume data. Information that is used for locating the sectioning plane and for processing the results can be obtained from 2D images generated from the 3D volume image.

The sequence of FIGS. 6E through 6H shows an alternate method for primary axis identification using sectioning by two or more planes.

Figure 6E:
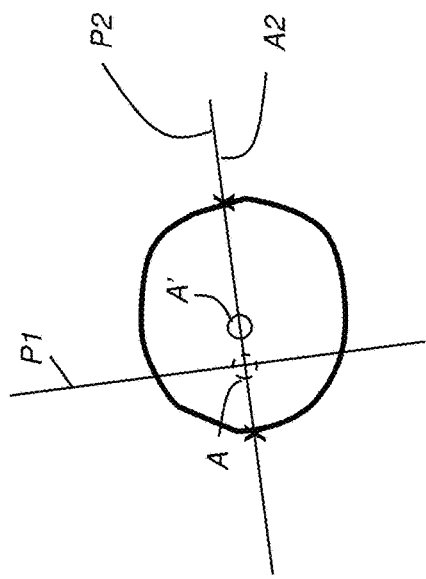
FIGS. 6E through 6H show alternate steps used for iterative axis reconstruction.
Figure 6F:
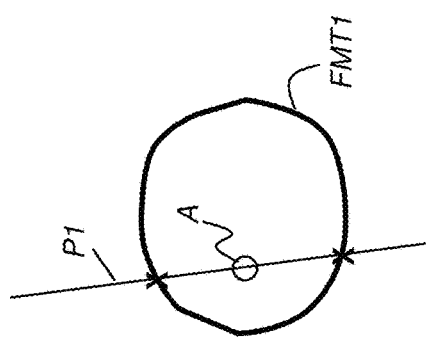

FIG. 6E shows the same initial sectioning by plane P1 that was executed in FIG. 6A. FIG. 6F shows how the iterative axis construction proceeds. From plane P2, it is clear that the initial axis A position must be adjusted with respect to axis A2 in sectioning plane P2. Corrected axis position A' lies closer to the geometric center axis of the bone than the original axis A estimate.

Figure 6H:
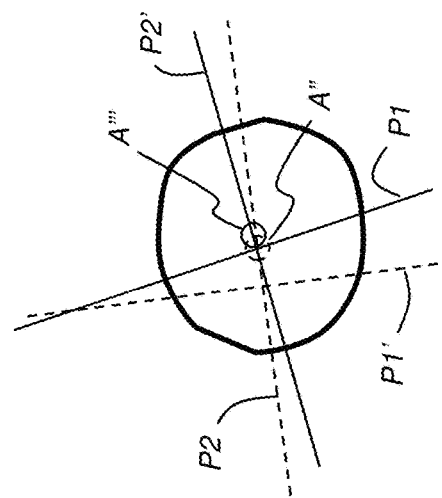
Figure 6G:
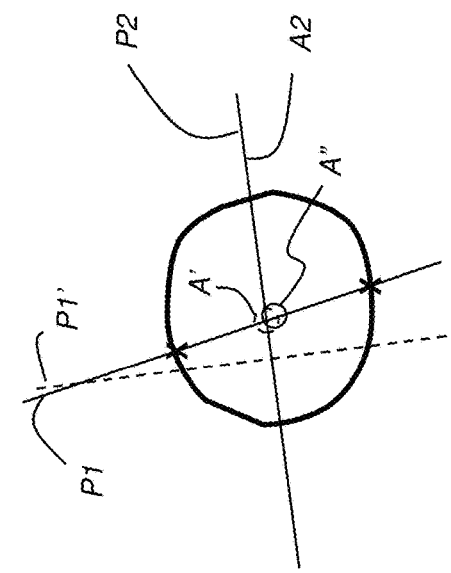

FIG. 6G shows an adjustment made to initial sectioning plane P1 position (shown in dashed lines) to construct plane P1' according to the adjusted axis A' position. With this adjustment, as part of the iterative process, the axis A' position may be refined, shown in this example as axis A". In FIG. 6H, repositioning of previous sectioning plane P2 to construct sectioning plane P2' causes another evaluation of axis A" positioning, and incremental adjustment to define axis A'.

It should be emphasized that the processes shown in FIGS. 6A-6D and FIGS. 6E-6H can be a simplification of the sectioning plane construction process used to show iteration for axis identification. As can be seen from these schematic sequences, iterative axis construction begins with plane sectioning to obtain a first approximation and successively improves position accuracy with each subsequent sectioning iteration, continually reducing the detected error in progressing from the previously calculated to a newly constructed axis A definition. In order to more closely approximate the 3D axis orientation, the procedure described in the sequences of FIGS. 6A-6D and FIGS. 6E-6H can be repeated as many times as needed until a suitable axis for the subject bone of interest is identified.

It should be noted that axis position can vary for a bone, depending on factors such as which cross-section is used (FIG. 4D), number of iterations desired, and allowable error tolerances, for example. As stated earlier, the initial estimation can be done using different approaches for different bones, for example, using projections of the whole volume, partial volume or using a selected slice from the 3D images, yielding a good first approximation.

Axis Definition for More Complex Bone Structures

An initial approximation for the primary axis and for positioning the first sectioning plane P1 can be obtained using a number of different techniques. FIGS. 4A-4C show initial axis approximation using a generated projection view of the volume data. This approach can be most workable where the primary axis corresponds to a longitudinal axis, such as for metatarsals and other bones that exhibit a generally lengthwise extension and that are relatively narrow. However, for bones that do not have a predominantly lengthwise extension, such as the talus, primary axis approximation and iterations are necessarily less exact and, because articular surfaces may not lie conveniently along the same axis, some compromises may need to be made.

For any bone, it is generally most useful and informative for the primary axis to extend through the bone from one articular surface to another and to be equidistant from outer surfaces of the bone at every point along the axis. This idealized arrangement, although it can be approximated for simpler skeletal structures, is simply not possible for some bone structures, particularly for bones having three or more articular surfaces, such as bones within complex joints for extremities. To generate a suitable primary axis to aid patient assessment and segmentation in these special cases, any of a number of alternative techniques can be used.

The identification of primary axes is helpful for analyzing overall bone and joint condition. However, it should be noted that there are no rigid definitions or standardized metrics that apply for identifying the primary axis for particular bone structures. It should be noted that the axis constructed using the methods described herein as primary axis for a bone is not necessarily an axis of symmetry, nor is the defined axis that is considered the primary axis, constructed as described herein, necessarily defined by centers of overall mass or volume. The primary axis that is identified using procedures described herein is generated according to individual patient anatomy and provides a convenient reference tool for subsequent segmentation and, apart from segmentation, for assessment of joint condition and related bone metrics. For some purposes, different axes can be constructed for analysis with more complex bones, based on the particular requirements of patient assessment and treatment.

Figure 7A:
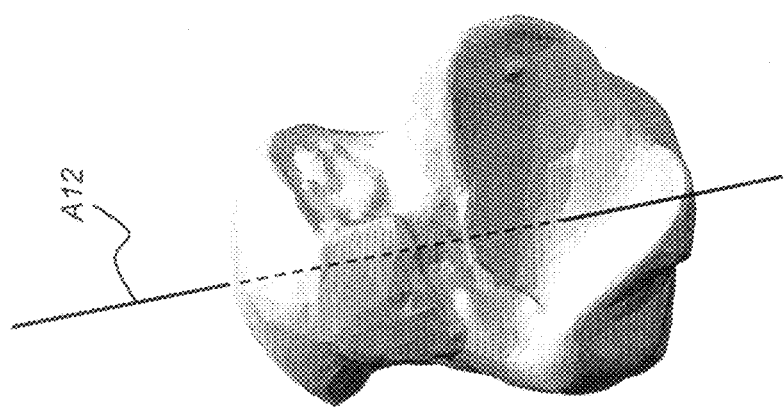
FIG. 7A shows an axis extending through a talus bone of the lower foot.
Figure 7B:
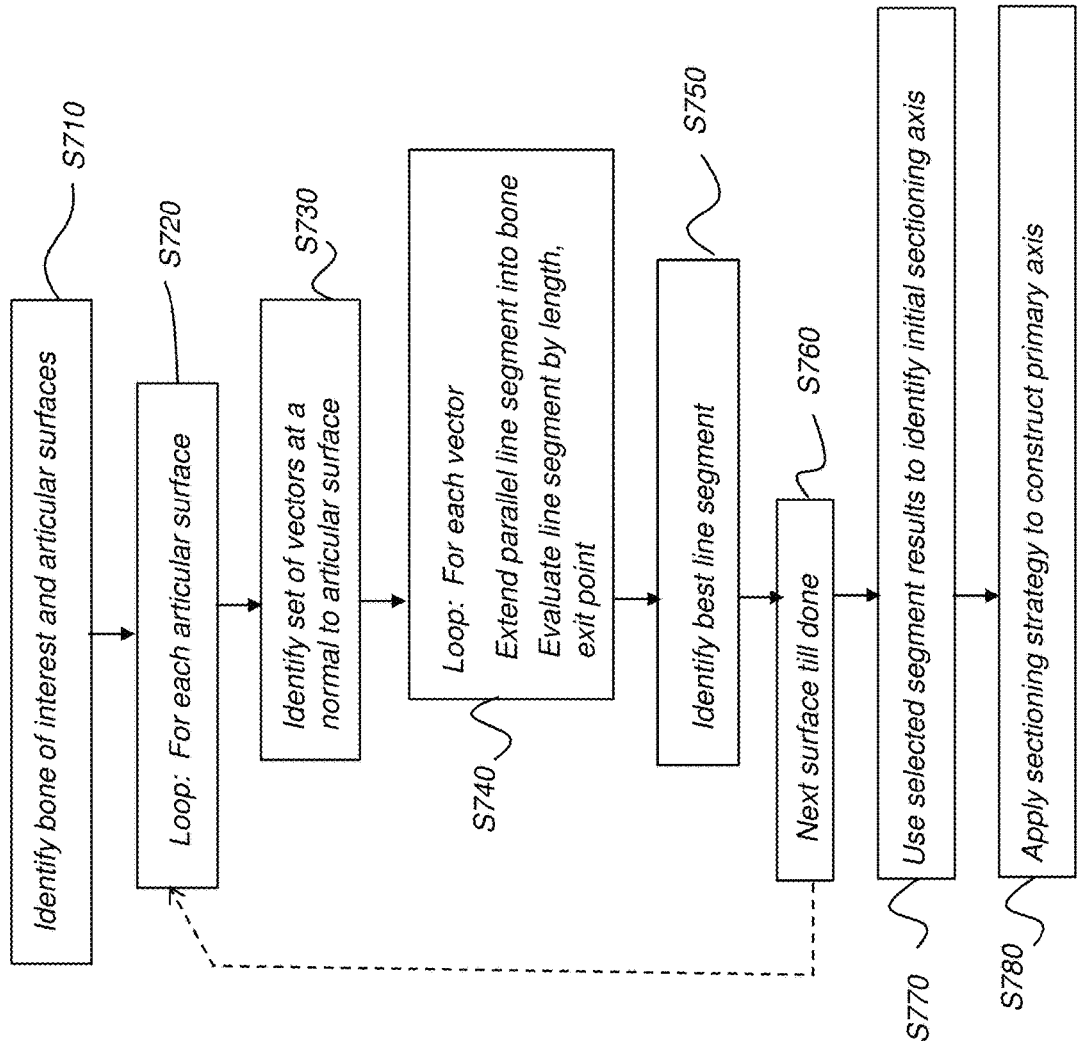
FIG. 7B is a logic flow diagram showing steps for identifying a primary axis according to an embodiment of the present disclosure.

By way of example related to bones of the lower foot, FIG. 7A shows a defined axis A12 extending through a talus bone. For this type of bone, bone shape may provide few hints for suitable axis orientation. More than two articular surfaces can be provided, with surfaces not disposed in a straightforward linear arrangement. One method for defining a primary axis for this type of complex bone shape is based on analysis of articular surfaces, as shown in FIG. 7B.

An identification step S710 identifies a bone of interest and its various articular surfaces. A looping step S720 then analyzes candidate line segments formed at each articular surface. In a vector identification step S730, a set of vectors that extend from the articular surface at a normal is identified. These vectors can help to locate line segments that extend in the direction of the desired axis. A vector looping step S740 describes one type of analysis for line segment evaluation. For each vector, a parallel line segment is extended back into the bone. This segment can be evaluated based on relative length; if the segment exits the bone too early, it is unlikely that the segment provides a promising candidate for further sectioning procedure to locate the axis. Segment length and exit point are factors that can be used for this evaluation. A particular segment that exits at a different articular surface can be more useful than a segment that exits the bone at some other point. A segment identification step S750 selects the best line segment for initial sectioning to identify the primary axis. A repeat step S760 repeats the process beginning with looping step S720. A segment combination step S770 uses the combined selected segment results to identify the initial axis for plane sectioning, as described previously. This can mean forming an initial sectioning axis using intersection points between various line segments or forming a line segment by averaging or otherwise combining the obtained line data. A sectioning step S780 then applies the iterative plane sectioning technique described previously in order to construct the primary axis.

Using Bone Features

An alternative method for axis identification uses well-known bone features as anchor points for the particular bone of interest. Anchor points can be used in conjunction with plane sectioning, as described previously and can also be used in conjunction with lines extended through and between articular surfaces as described with reference to FIG. 7B. Bone features data can be obtained and stored from a priori knowledge of anatomy, such as from atlas information or population data.

According to an alternate embodiment, axis definition can be obtained for articular surfaces that are paired with interfacing articular surfaces, as well as for articular surfaces independent of other cooperating surfaces. Bone structure for paired articular surfaces tends to be at least roughly symmetric about an axis. With such a structure, feature points can be obtained from analysis of both surfaces.

Figure 7C:
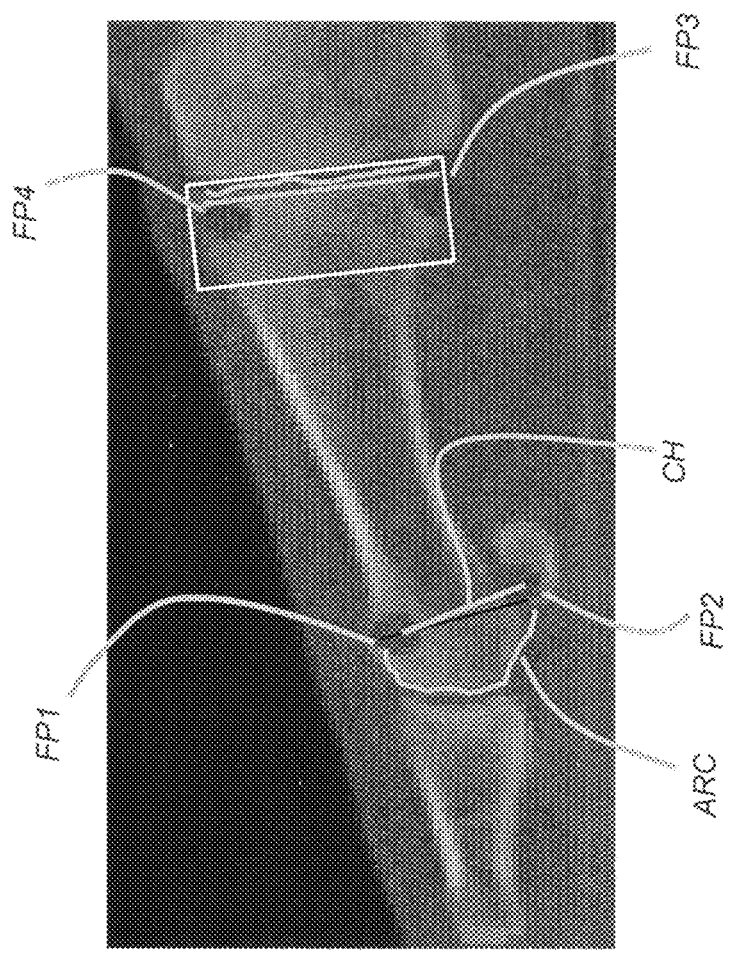
FIG. 7C shows feature points and geometric features that can be used for axis construction.

FIG. 7C shows feature points FP1-FP4 as well as an arc ARC along an articular surface and a chord CH to arc ARC that can be used as features for axis construction. The feature points FPn are used to determine points that can be used in order to construct a bisecting line in the 2D image. These feature points can be the end points of the arc, a line segment for the arc span such as the chord of a superimposed arc, or two or more line segments within an ROI. For a given articular surface, feature points from the analysis of the respective articular surface or its local neighborhood region can be used to determine the bisecting line.

FIG. 7D shows another example of feature points and geometric features that can be used for axis A construction. Initially, two feature points are located according to a detected arc defined along a bone joint. Then, the bone is further analyzed to obtain additional feature points that define the neck of the bone. Axis A can then be constructed through chord and line segment midpoints as shown.

Figure 8C:
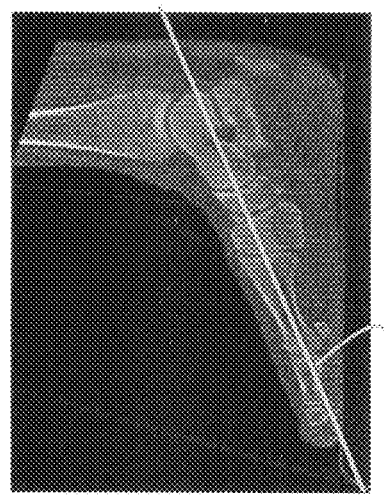
FIGS. 8A-8D show a sequence for axis location using feature points.
Figure 8B:
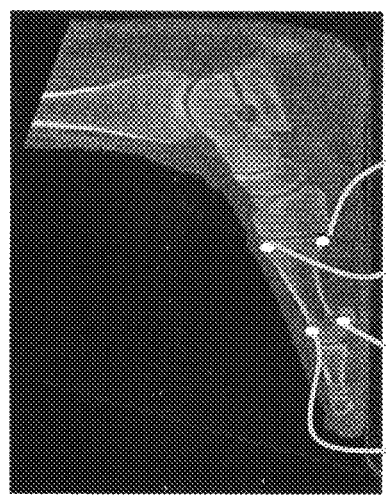
Figure 8A:
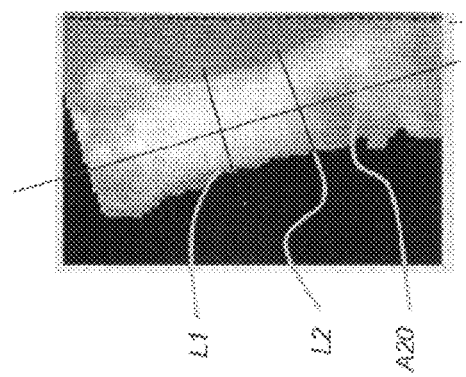
Figure 8D:
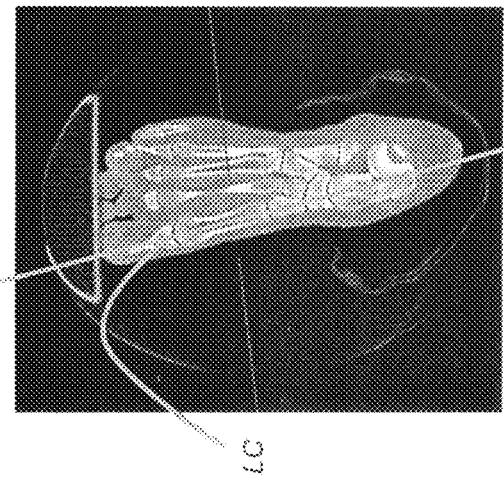

FIGS. 8A, 8B, 8C, and 8D show a sequence for primary axis construction using feature points according to an embodiment of the present disclosure. The basic sequence is parallel to the steps shown previously in FIGS. 6A-6D. FIG. 8A shows an initial axis A20 defined using the midpoints of line segments L1 and L2 as previously described. FIG. 8B shows feature points FP1, FP2, FP3, and FP4 identified in the generated projection image. FIG. 8C shows a center line LC constructed using the feature points. FIG. 8D is an axial generated projection view showing the position of the constructed center line LC.

Figure 9C:
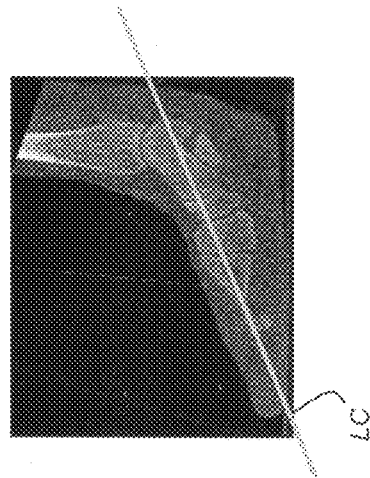
FIGS. 9A-9H show an alternate sequence for axis location using feature points.
Figure 9B:
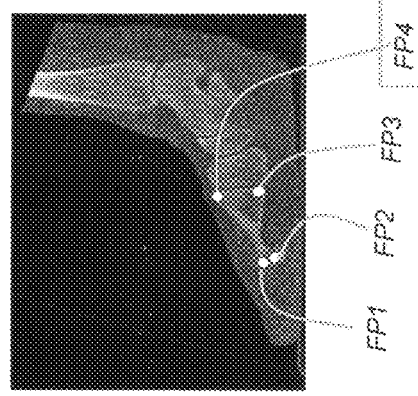
Figure 9D:
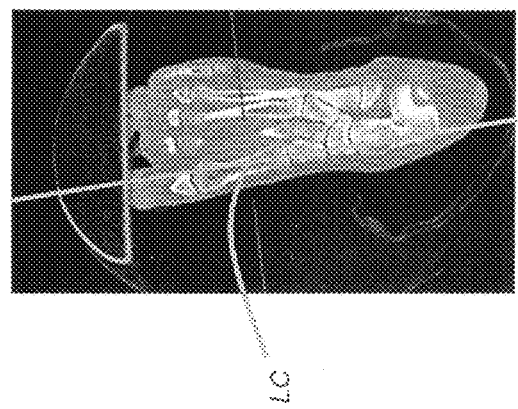
Figure 9A:
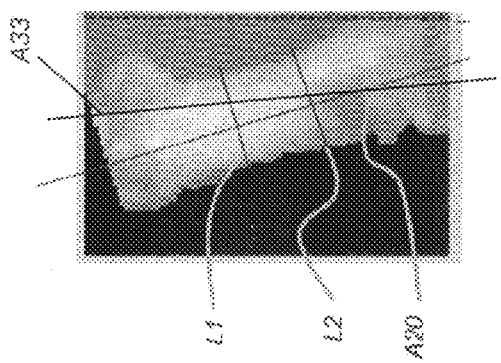
Figure 9G:
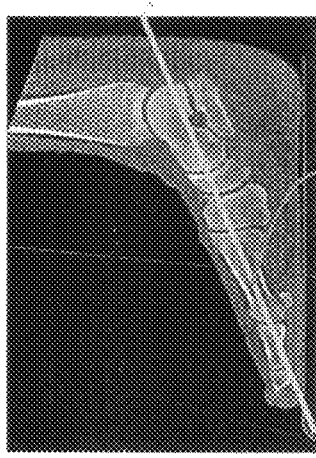
Figure 9F:
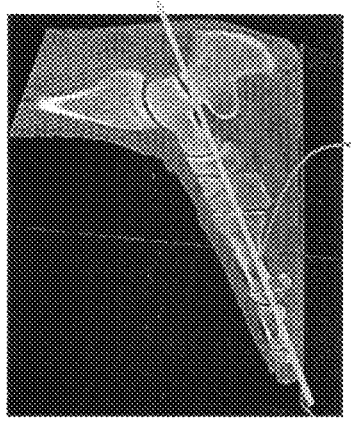
Figure 9E:
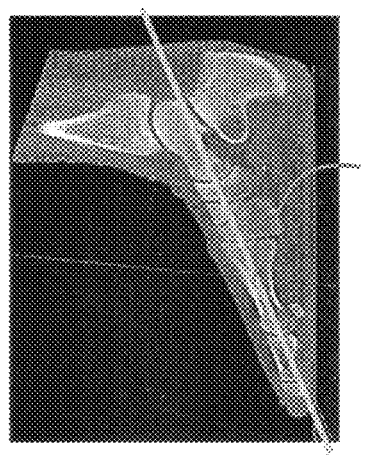
Figure 9H:
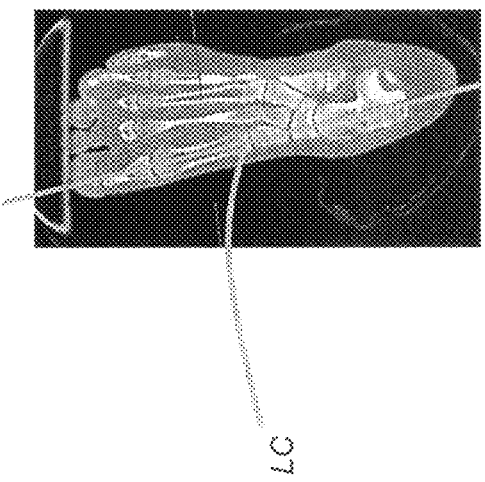

FIGS. 9A, 9B, 9C, 9D, 9E, 9F, 9G, and 9H show how the method of repeated sectioning using orthogonal planes can be successfully implemented, even where detection of feature points can be more challenging. The basic sequence is parallel to the steps shown previously in FIGS. 6E-6H. In FIG. 9A, a different line, perceptibly off center, is selected as the initial axis A33. FIG. 9B shows results of sectioning sagittal plane P1 and identification of feature points FP1, FP2, FP3, and FP4. FIG. 9C shows construction of center line LC according to the identified feature points. FIG. 9D is an axial generated projection view, following sectioning by axial plane P2, showing the position of center line LC. FIGS. 9E, 9F, 9G, and 9H then show results of further sectioning by sagittal and axial planes P1' and P2' for refining the definition of center line LC.

Axis Identification Using Machine Learning

Machine learning techniques can be used in conjunction with the analysis described herein for determining the most suitable primary axis for a particular bone.

According to an alternate embodiment of the present disclosure, the construction of a primary axis can be assisted by the user, who can make adjustments to the line, defining particular points through which center line LC is constructed. This allows the practitioner to fine-tune the automated line LC construction, which can be useful where bone structures may not be readily detectable using algorithmic methods.

Surface Characterization

Once the primary axis A position is defined to within acceptable tolerances, the constructed primary axis A can be used for segmentation and measurement functions. Using the example for first metatarsal FMT1 described in preceding FIGS. 4A-6D, FIGS. 10A, 10B, and 10C show how primary axis A can be used for surface characterization according to an embodiment.

Figure 10C:
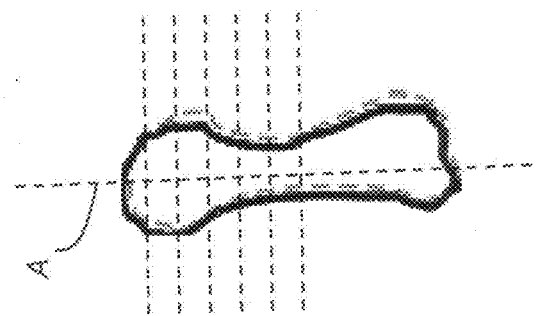
FIGS. 10A through 10C show processing steps for segmentation of a bone of the foot.
Figure 10B:
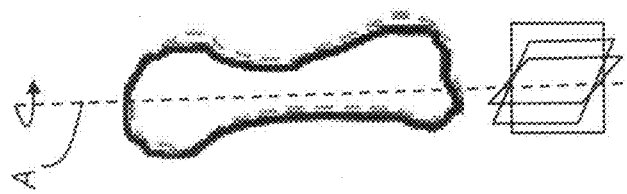
Figure 10A:
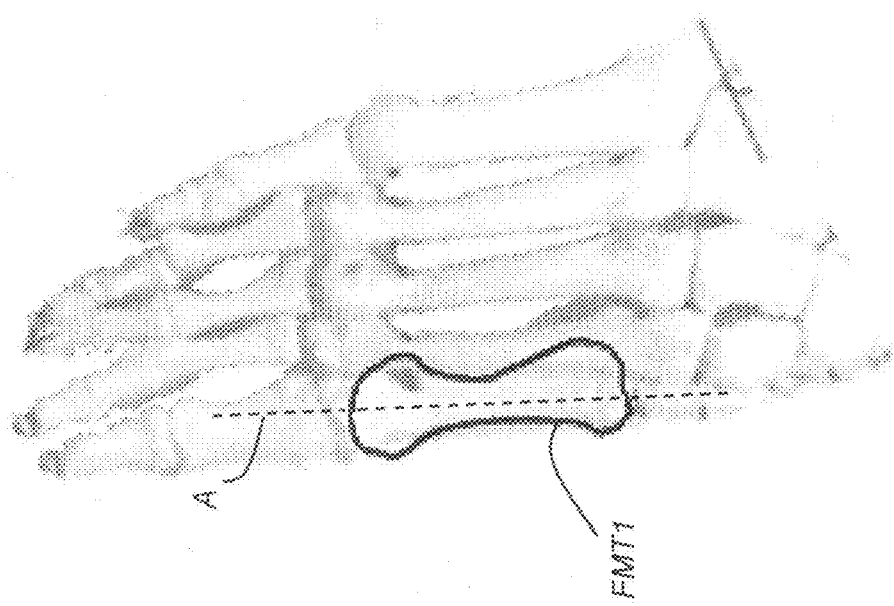

In the example of FIG. 10A, first metatarsal FMT1 is shown in outline, superimposed over a projection of the image volume and showing axis A, constructed using the approach described previously. The goal of segmentation is to isolate bone FMT1 from its surrounding bone structures, such as to separately display the first metatarsal structure and surfaces in order to allow more careful examination.

An approach for segmentation of a skeletal component such as the first metatarsal FMT1 is to form a surface contour by a repeated sequence of defining the surface outline within a plane, then incrementally using rotation of the plane about the constructed axis A. As is shown in FIG. 10B, the surface contour of the bone changes relatively slowly with incremental rotation about a well-constructed axis A, helping to simplify the computational task of edge detection at successive rotational angles. As shown in FIG. 10C, measurements can be acquired at positions along the constructed axis A, such as at cross-sectional positions with respect to axis A.

Figure 11:
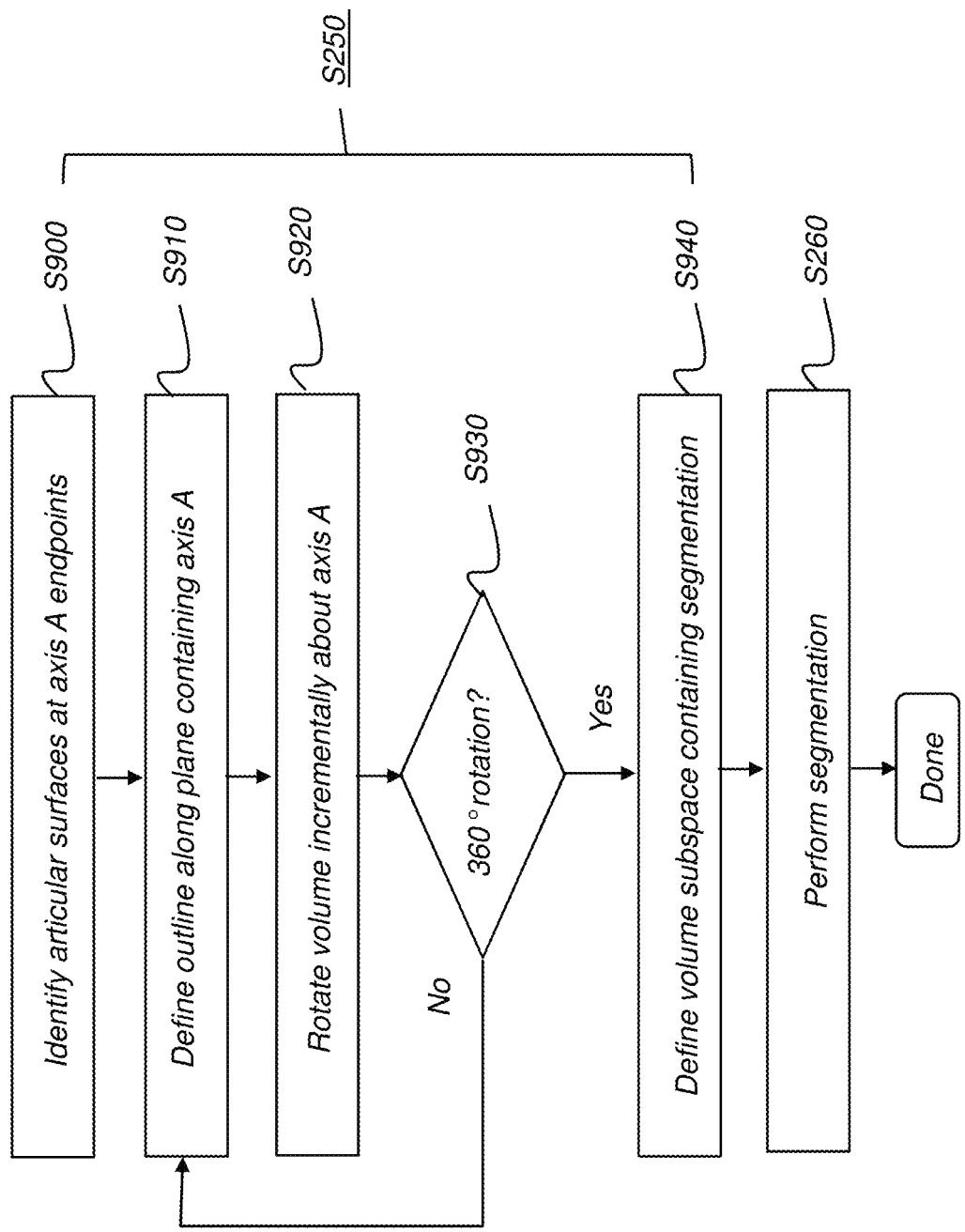
FIG. 11 is a logic flow diagram showing a sequence for defining a subspace of the reconstructed volume that has the desired segmentation for a bone feature.

The set of outline definitions that are obtained using rotation about axis A can then be combined to perform segmentation. The logic flow diagram of FIG. 11 shows a sequence for defining a subspace of the reconstructed volume that has the desired segmentation for a bone feature. In a surface identification step S900, articular surfaces at endpoints of the bone are identified. This provides a coarse bounding of the segmented bone with respect to the constructed axis, even where portions of the articular surface extend further with respect to the axis A. An outlining step S910 then defines an outline for the bone with respect to a plane that includes the axis A. A rotation step S920 then rotates the plane view relative to axis A. A decision step S930 determines whether or not full 360 degree rotation has been implemented. If not, the bone outline is determined in step S910 and rotation continues in step S920. If full rotation has been executed, or the rotation used is sufficient for defining the bone outline for segmentation, the individual outlines from the full set of rotation angles are combined in a subspace definition step S940. With the subspace defined, segmentation of the reconstructed volume can be executed in step S260.

Articular Surface Definition

Figure 12B:
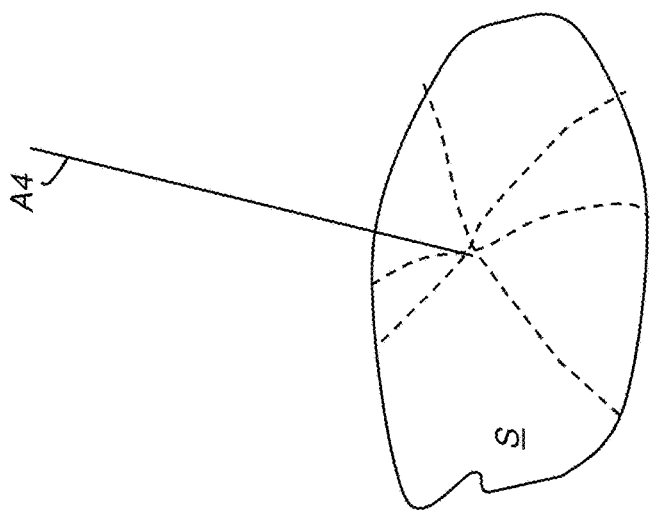
FIGS. 12A and 12B show features of articular surface segmentation.
Figure 12A:
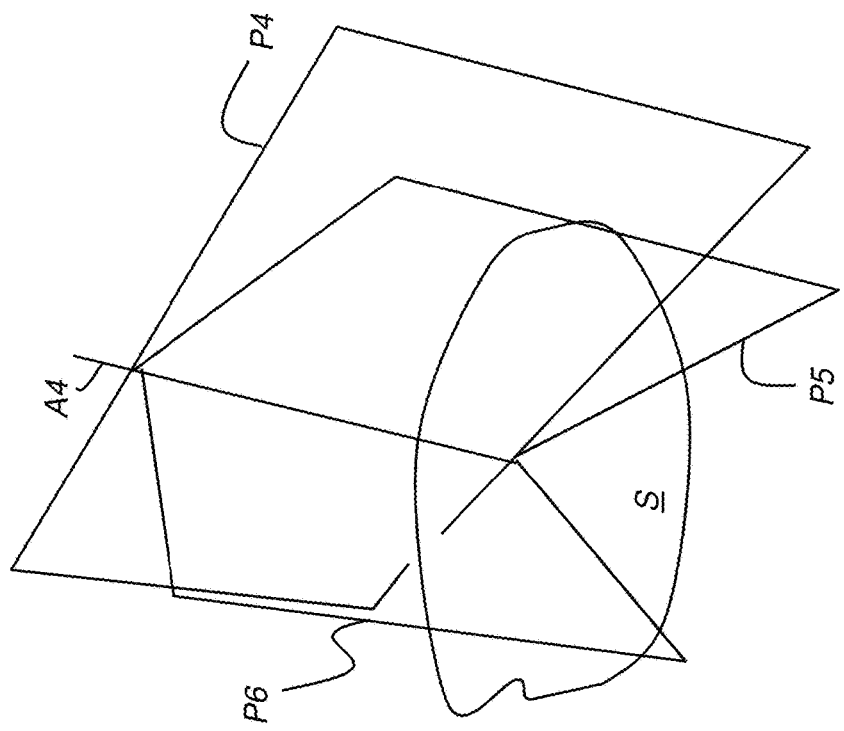

Accurate profiling of the articular surfaces of bones can be particularly useful for diagnostic assessment of arthritis and other joint-related conditions. FIG. 12A shows an axis A4 extended in an orthogonal direction from a point on an articular surface S. Using a succession views from planes P4, P5, and P6 rotated about axis A4, for example, the surface contour of articular surface S can be reconstructed. Articular surface definition achieved in this manner is shown in FIG. 12B.

Segmentation

Segmentation step S260 of FIG. 2 can employ the surface definition described with reference to FIGS. 10A-10C along with other segmentation methods. These can include definition of seed points and growing from the seed points. Seed points can be determined, for example, by identifying gradients or particular points of high density, then by assigning one or more high density pixels or voxels as seed points for further processing.

Edge Refinement

Edge detection methods can be used to more accurately define bone edges in the above sequence for segmentation.

These edge refinement techniques can include gradient analysis, determining continuous features, and other techniques, for example.

Figure 13A:
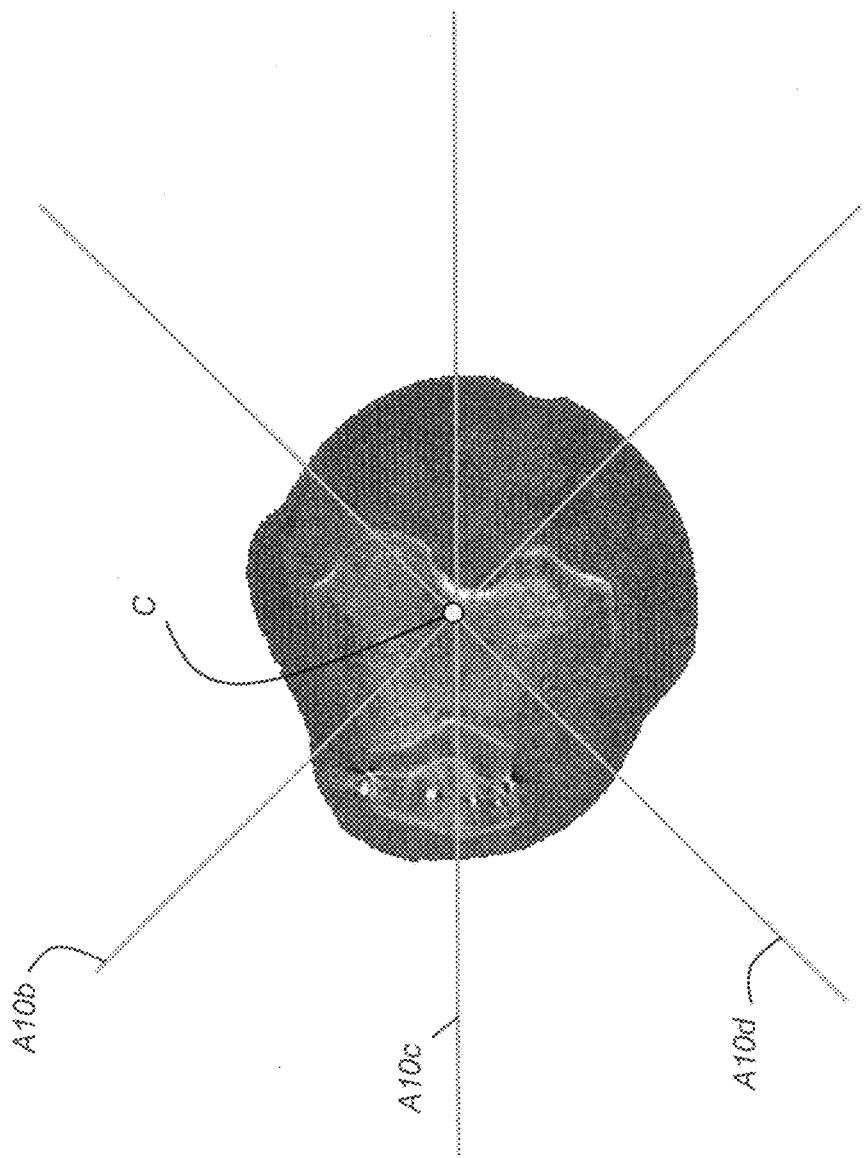
FIG. 13A shows an axial slice of a reconstructed knee volume.
Figure 13D:
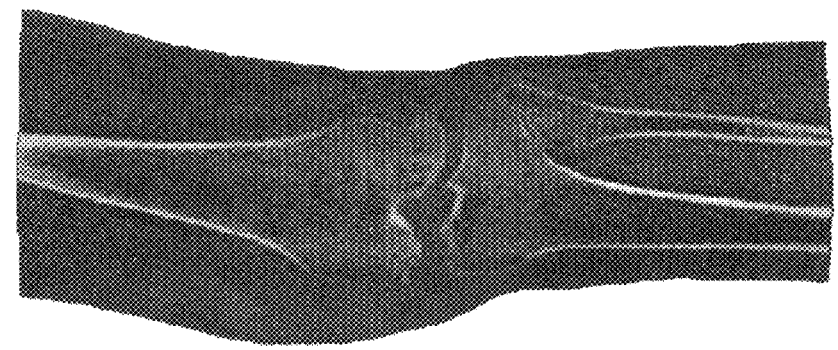
FIGS. 13B through 13D show different views of the knee volume rotated about a common axis.
Figure 13C:
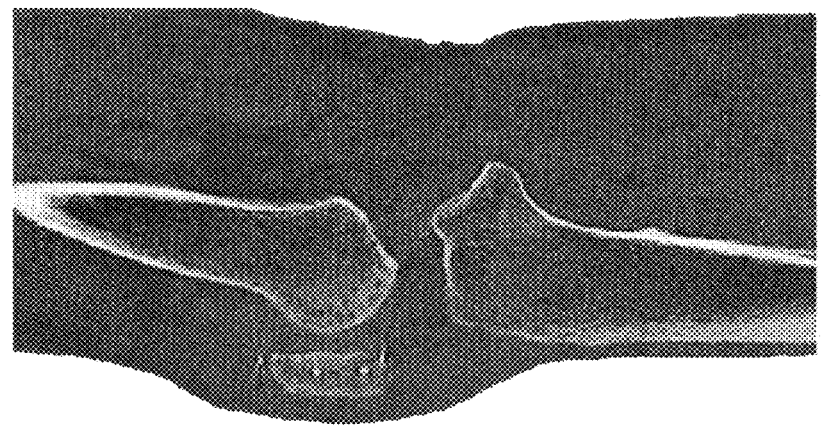
Figure 13B:
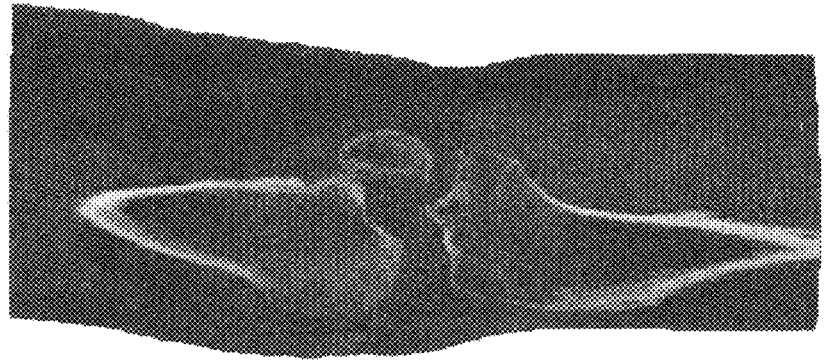

The example of FIG. 13A shows an axial view of the knee joint. Three axes A10b, A10c, and A10d, corresponding to FIGS. 13B, 13C, and 13D respectively, show different slices of the reconstructed volume of the knee, with the views rotated about a center C. It can be appreciated that the different respective views allow relatively straightforward combination of bone profile information when rotated about a suitable axis.

Identification of the primary axis can use plane sectioning with the pattern shown in FIG. 13A. However, use of mutually orthogonal sectioning planes, as described previously, is advantaged for more straightforward processing.

Axes Angular Relationships

The relative angular relationships of adjacent or intersecting bone axes constructed as described herein can serve as useful metrics for diagnosis of conditions related to overall joint function.

Figure 14:
FIG. 14 shows an exemplary view of an operator interface that displays a volume image and view slices from appropriate angles.

FIG. 14 shows an exemplary view of an operator interface that displays a volume image and shows view slices rendered from appropriate angles. According to an embodiment of the present disclosure, an operator instruction, such as a command entered on the operator interface screen, initiates detection and display of the primary axis, using procedures described herein. Exemplary command buttons 40 are shown at the upper left portion of the screen. These can include auxiliary instructions, such as for viewer annotation or on-screen measurement between selected feature points, for example.

Figure 15:
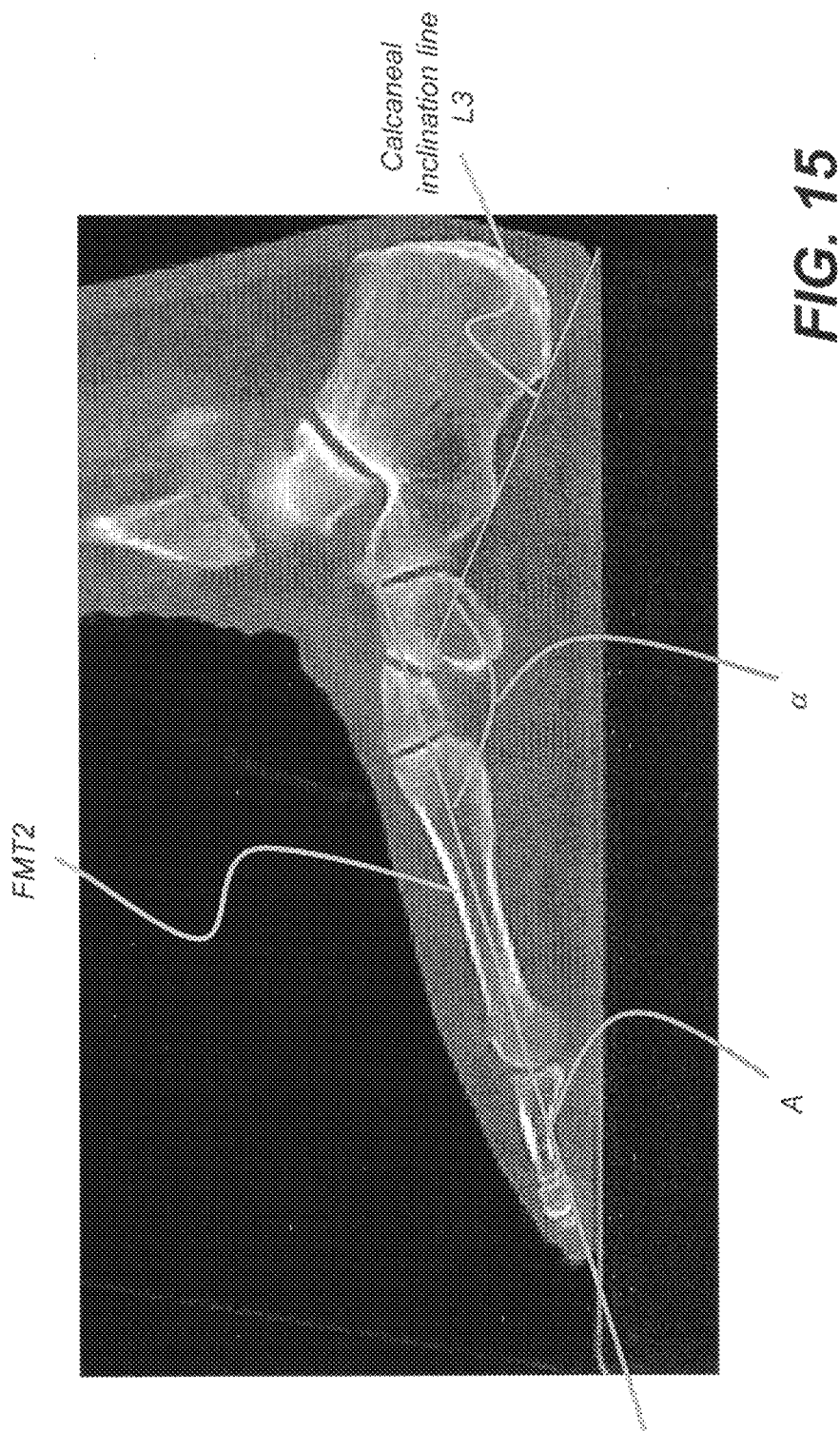
FIG. 15 shows a slice that includes the second metatarsal FMT2 and connected bone features.

FIG. 15 shows a rendered slice that includes the second metatarsal FMT2 and connected bone features. This example shows how a slice image can be used to identify and display a metric or orientation feature, here the calcaneal inclination line L3, used to determine a calcaneal inclination angle. By way of example, an angle $\alpha$ is shown between line L3 and a constructed primary axis A for a metatarsal bone.

Joint spacing measurements can also be obtained and displayed using segmentation of adjacent bone features.

Advantageously, the defined axes for bones can be displayed in 3D, as part of the reconstructed 3D volume image or separate from the image content. 3D views can then be rotated on the display in order to allow the practitioner to view angular relationships from a number of perspectives and to measure characteristics such as azimuth and zenith angles relative to a standard view or coordinate assignment.

FIG. 16 shows segmentation examples for a joint that can be obtained using methods of the present disclosure.

Consistent with one embodiment of the present disclosure, the present disclosure utilizes a computer program with stored instructions that perform on image data accessed from an electronic memory. As can be appreciated by those skilled in the image processing arts, a computer program of an embodiment of the present disclosure can be utilized by a suitable, general-purpose computer system, such as a personal computer or workstation. However, many other types of computer systems can be used to execute the computer program of the present disclosure, including networked processors. The computer program for performing the method of the present disclosure may be stored in a computer readable storage medium. This medium may comprise, for example; magnetic storage media such as a magnetic disk such as a hard drive or removable device or magnetic tape; optical storage media such as an optical disc, optical tape, or machine readable bar code; solid state electronic storage devices such as random access memory (RAM), or read only memory (ROM); or any other physical device or medium employed to store a computer program. The computer program for performing the method of the present disclosure may also be stored on computer readable storage medium that is connected to the image processor by way of the internet or other communication medium. Those skilled in the art will readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Displaying an image requires memory storage. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present disclosure may make use of various image manipulation algorithms and processes that are well known. It will be further understood that the computer program product embodiment of the present disclosure may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present disclosure, are not specifically shown or described herein and may be selected from such algorithms, systems, hardware, components and elements known in the art.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A computer implemented method comprising the steps of:

accessing a reconstructed 3D tomographic volume image of a patient anatomy;

identifying a bone in a 2D projection image of the accessed volume image of the patient anatomy;

constructing a primary axis for the bone, comprising the steps of:

determining a plurality of lines across the bone from one edge of the bone to an opposite edge in the 2D projection image of the bone and determining a midpoint for each of the plurality of determined lines;

estimating the primary axis as a line through the determined plurality of midpoints or, if the determined plurality of midpoints are not collinear, as a best fit line calculated for the determined plurality of midpoints;

determining a first sectioning plane in a plane of the estimated primary axis and determining a second sectioning plane in another plane of the primary axis, the second sectioning plane orthogonal to the first sectioning plane;

determining a midpoint between edges of the bone in the first sectioning plane and determining a midpoint between edges of the bone in the second sectioning plane; and reestimating the primary axis as a line through the determined midpoint between edges of the bone in the first sectioning plane and the determined midpoint between edges of the bone in the second sectioning plane; and displaying, storing, or transmitting the reestimated primary axis for the bone.

2. The method of claim 1, wherein the first sectioning plane is perpendicular to a plane of the 2D projection image.

3. The method of claim 2, further comprising forming the 2D projection image using only a portion of the reconstructed 3D tomographic volume image of the patient anatomy.

4. The method of claim 2, further comprising forming the 2D projection image using only a single image slice of the reconstructed 3D tomographic volume image of the patient anatomy.

5. The method of claim 1, further comprising segmenting the bone within the volume image of the patient anatomy.

6. The method of claim 1, further comprising identifying two or more features of the bone.

7. The method of claim 6 wherein the two or more features include an articular surface.

8. The method of claim 1, wherein the step of determining a midpoint between edges of the bone in the second sectioning plane comprises identifying two or more features of the bone in the first sectioning plane.

9. The method of claim 1, further comprising:
determining a third sectioning plane orthogonal to the second sectioning plane; and
reestimating the primary axis according to an image of the bone in the third sectioning plane.

10. The method of claim 1 further comprising measuring and reporting, on a display, a length of the primary axis.

11. The method of claim 1, further comprising displaying one or more of axis length and axis angle of the primary axis.

12. The method of claim 1, further comprising accepting an operator instruction to reposition the primary axis.

13. The method of claim 1, further comprising displaying the primary axis in 3D space.

14. The method of claim 1, further comprising displaying two or more primary axes in 3D space.

15. The method of claim 14, further comprising displaying an angle between the displayed two or more primary axes.

16. A computer implemented method comprising:
accessing a reconstructed 3D tomographic volume image of a patient anatomy;
using the 3D tomographic volume image, forming a 2D projection image of the 3D tomographic volume image;
identifying four or more feature points of a bone within the 2D projection image;
defining a primary axis for the bone as a line that passes through midpoints of a plurality of line segments each extending between a distinct pair of the identified feature points or as a best fit line calculated for the midpoints of the plurality of line segments;
sectioning the 3D tomographic volume image according to a first sectioning plane along the defined primary axis;
sectioning the 3D tomographic volume image according to a second sectioning plane orthogonal to the first sectioning plane containing the defined primary axis;
redefining the defined primary axis according to a position of the bone relative to the defined primary axis in the second sectioning plane; and
displaying, storing, or transmitting the redefined primary axis for the bone.

17. A computer implemented method comprising:
accessing a reconstructed 3D tomographic volume image of a patient anatomy;
forming a 2D projection image of the 3D tomographic volume image, the 2D projection image including a bone;
constructing a primary axis extending through the bone using an iterative process that repeats the steps of:
using a plane extending in a first direction, sectioning the 3D tomographic volume image along a calculated primary axis, including determining a plurality of bone widths along the bone, calculating midpoints of each of the plurality of bone widths, determining a line through the plurality of midpoints and defining the calculated primary axis as the determined line through the plurality of midpoints;
using a plane extending in a second direction orthogonal to the first direction, sectioning the 3D tomographic volume image along the calculated primary axis; and
adjusting the position of the calculated primary axis according to a position of the bone relative to the calculated primary axis in the sectioning by the mutually orthogonal planes; and
displaying, storing, or transmitting the adjusted calculated primary axis for the bone of interest.

18. The method of claim 16, further comprising:
determining a third sectioning plane orthogonal to the second sectioning plane and determining a position of the bone relative to the defined primary axis in the third sectioning plane.

19. The method of claim 16, further comprising:
displaying the redefined primary axis in 3D space.

20. The method of claim 17, further comprising:
determining a third sectioning plane orthogonal to both of the mutually orthogonal planes and determining the position of the bone relative to the calculated primary axis in the third sectioning plane.

* * * * *